United States Patent [19]
Golightly et al.

[11] Patent Number: 6,033,891
[45] Date of Patent: Mar. 7, 2000

[54] NUCLEIC ACIDS ENCODING POLYPEPTIDES HAVING CELLOBIOSE DEHYDROGENASE ACTIVITY

[75] Inventors: Elizabeth Golightly, Davis; Kimberly Brown, Elk Grove, both of Calif.

[73] Assignee: Novo Nordisk Biotech, Inc., Davis, Calif.

[21] Appl. No.: 09/265,108

[22] Filed: Mar. 9, 1999

[51] Int. Cl.[7] .............................. C12N 9/04; C12N 15/00; C12N 1/20; C12Q 1/68; C07H 21/04

[52] U.S. Cl. ...................... 435/190; 435/252.3; 435/325; 435/320.1; 435/6; 536/23.2

[58] Field of Search ................. 435/190, 320.1, 435/325, 252.3, 6, 23.2

[56] References Cited

U.S. PATENT DOCUMENTS 5,866,392  2/1999  Schou et al. ............................ 435/190

OTHER PUBLICATIONS

Westermark & Eriksson, 1974, Acta Chem. Scand. Ser. B28: 204–208.
Westermark & Eriksson, 1974, Acta. Chem. Scand. Ser. B28: 209–214.
Ayers et al., 1978, European Journal of Biochemistry 90: 171–181.
Schmidhlater & Canevascini, 1992, Applied Microbiology Biotechnology 37: 431–436.
Dekker, 1980, Journal of General Microbiology 120: 309–316.
Fähnrich & Irrgang, 1982 Biotechnology Lettters 4: 775–780.
Coudrray et al., 1982 Biochemical Journal 203: 277–284.
Sadana & Patil, 1985, Journal of General Microbiology 131: 1917–1923.
Schou et al., 1998, Biochemical Journal 330: 565–571.
Raices et al., 1995, FEBS Letters 369: 233–238.

*Primary Examiner*—Ponnathapu Achutamurthy
*Assistant Examiner*—M. Monshipouri
*Attorney, Agent, or Firm*—Steve Zelson, Esq.; Elias Lambiris, Esq.; Robert L. Starnes

[57] ABSTRACT

The present invention relates to isolated nucleic acid sequences encoding polypeptides having cellobiose dehydrogenase activity. The invention also relates to nucleic acid constructs, vectors, and host cells comprising the nucleic acid sequences as well as recombinant methods for producing the polypeptides.

28 Claims, 5 Drawing Sheets

```
AGCTACAGCTTCCTTGGGCCCGTCTGAACCAACCTTCTGGGACCAAGTGTGAGATCTGGCGGCACAACC   70
ATGAAGTTCCTGGCCTCGGCCGTATTGGGGCGACCGCCCTTGCGCGCCCTCGTCGCTTCACATCAGGCCCGCGC  140
 M  K  F  L  G  R  I  G  A  T  A  L  A  A  S  L  Y  L  T  S  G  A  A
AAGCCACTGGTGATGCGTACACCGACTCGGAAACAGGCATTAAGTTCCAGACCTGGTCCCCGGATCCGCA  210
 Q  A  T  G  D  A  Y  T  D  S  E  T  G  I  K  F  Q  T  W  S  P  D  P  Q
GTTCACTTTTGGCCTTGCGCCGGATGCCCTGCCGCCGGATGCCCTGGAGAAGGATGCCACTGAGTACATTGGTCTTCTC  280
 F  T  F  G  L  A  L  P  P  D  A  L  E  K  D  A  T  E  Y  I  G  L  L
CGCTGCACCAGGGCCGACCCATCCGACCCTGGCGTCTCTCATGGCCAGGTCGGCCAGATGA  350
 R  C  T  R  A  D  P  S  D  P  G  Y  C  G  L  S  H  G  Q  V  G  Q  M
CGCAGTCGCTGCTTCGTCGTGGCCTAGCCAGTCTCTACACGTCGTTCCGCTACGCCACCGG  420
 T  Q  S  L  L  V  A  W  A  Y  E  N  Q  V  Y  T  S  F  R  Y  A  T  G
CTACACCCCCGGGTCTCGTACACCAGCTCTCCGTCAACATCACCGACACC  490
 Y  T  L  P  G  L  Y  T  G  N  A  K  L  T  Q  L  S  V  N  I  T  D  T
AGCTTCGAGCTCATCTACCGCTGCGAGAACTGCTCTTCGTGGGAGCACGAAGGCAGCACCGGATCTAGCT  560
 S  F  E  L  I  Y  R  C  E  N  C  F  S  W  E  H  E  G  S  T  G  S  S
CGACCCTCCCAGGCTATCTCGTTCTGGGCCGCGCGTCGTCGCGGCGACTTGCCC  630
 D  P  P  Q  G  Y  L  V  L  G  R  A  S  A  R  R  G  V  G  P  T  C  P
GGACACGGCCACCTTTGGTTTCCACGACAATGGCTTCGGTCAGTGGGGTGTTGGTCTCGAGAATGCCGTT  700
 G  E  A  Q  C  V  P  A  P  E  E  T  Y  D  Y  I  V  V  G  A  G  A  G
TCGGAGCAGTATTCTGAGTGGGCTTCGCTGCCGGGTCTGTTGAGACCACCTGTGAAGGATCCGGCC  770
 S  E  Q  Y  S  E  W  A  S  L  P  G  L  T  V  E  T  T  C  E  G  S  G
CTGGTGAGGCGCAGTGCGTGCCCTGCCCTGAGGAGACTTATGACTATATTGTTGTTGGTGCCGGG  840
 P  G  E  A  Q  C  V  P  A  P  E  E  T  Y  D  Y  I  V  V  G  A  G  A  G
CGGTATTCCTGTCGCGCCGACAAGCTGAGCGAGGCCGGCCACAAGGTTCTGCTCATCGAGAAGGGTCCCCCG  910
 G  I  P  V  A  D  K  L  S  E  A  G  H  K  V  L  L  I  E  K  G  P  P
```

```
TCGACGGGGCCGCTGGCAGGGTACCATGAAGCCCGAGTGGCTTGAAGGCACTGACCTCACTCGGTTCGATG  980
 S  T  G  R  W  Q  G  T  M  K  P  E  W  L  E  G  T  D  L  T  R  F  D
TGCCCGGCCTTTGCAACCAGATCTGGGTTGACTCGGCTGGCATTGCCTGCACTGATACTGATCAGATGGC  1050
 V  P  G  L  C  N  Q  I  W  V  D  S  A  G  I  A  C  T  D  T  D  Q  M  A
TGGCTGCGTCTTGGGCGGTGCCACGGCCGTTAATGCTGGCCTGTGGAAGCCCATTGACCTCGACTGG  1120
 G  C  V  L  G  G  G  T  A  V  N  A  G  L  W  K  P  I  D  L  D  W
GATGAGAACTTCCCTGAGGGCTGGCACTCGCAGGATCTCGCCGCGGCCGCGACCGAGCGCGTCTTTGAGCGCA  1190
 D  E  N  F  P  E  G  W  H  S  Q  D  L  A  A  A  T  E  R  V  F  E  R
TCCCCGGCACCTGGCACCCGTCCATGGACGGCAAGCTGTACCGTGACGAAGGCTACAAGGTTCTCTCCAG  1260
 I  P  G  T  W  H  P  S  M  D  G  K  L  Y  R  D  E  G  Y  K  V  L  S  S
CGGTCTGGCTGAGTCTGGCTGGAAGGAGGTTGTGGCCAACGAGGTTCCCAACGAGAAGAACCGCACTTTC  1330
 G  L  A  E  S  G  W  K  E  V  V  A  N  E  V  P  N  E  K  N  R  T  F
GCCCACACCCACTTCATGTTCGCTGGCGGAGAGCGTAACGGGCCCTCTTGCCCACTTACCTGTCTCTGCCG  1400
 A  H  T  H  F  M  F  A  G  G  E  R  N  G  P  L  A  T  Y  L  V  S  A
ATGCCCGGAGAACTTCTCGCTTGGACCAACACTGCTGTTCGCCGCGCTGTTCGCCACTGGTGGCAAGGT  1470
 D  A  R  E  N  F  S  L  W  T  N  T  A  V  R  R  A  V  R  T  G  G  K  V
CACAGGTGTCGAGCTGGAGTGCTTGACTGATGGCGGCTACAGCGGCATTGTTAAGCTCAATGAGGGCGGT  1540
 T  G  V  E  L  E  C  L  T  D  G  G  Y  S  G  I  V  K  L  N  E  G  G
GGCGTCATCTTCTCGGCCGGTGCCTTTGGTTCGGCCAAGCTGCTCTTCCGCAGCGGTATCGGCCCTGAGG  1610
 G  V  I  F  S  A  G  A  F  G  S  A  K  L  L  F  R  S  G  I  G  P  E
ATCAGCTCCGCGTTGTTGCCTCCTCTAAGGACGGAGAGGACTTCATCGACGAGAAGGACTGGATTAAGCT  1680
 D  Q  L  R  V  V  A  S  S  K  D  G  E  D  F  I  D  E  K  D  W  I  K  L
CCCCGTCGGCTACAACCTGATTGACCACCTTAACACTGACCTCATCCTCACTCACCCCGATGTCGTCTTC  1750
 P  V  G  Y  N  L  I  D  H  L  N  T  D  L  I  L  T  H  P  D  V  V  F
```

```
TACGACTTCTATGAGGCCTGGACCACCCCGATCGAGGCCGACAAGCAGCTGTACCTTGAGCAGCGCTCTG  1820
 Y  D  F  Y  E  A  W  T  T  P  I  E  A  D  K  Q  L  Y  L  E  Q  R  S
GCATCCTTGCCCAGGCCGCTCCTAACATTGGCCCCATGATGTGGGAGCAGGTCACCCCCTCGGACGGCAT  1890
 G  I  L  A  Q  A  A  P  N  I  G  P  M  M  W  E  Q  V  T  P  S  D  G  I
TACCCGCCAATTCCAGTGGACCGCTCGCGTCGAGGGCGACAGCCGCTTCACCAACTCTTCATGCCATG   1960
 T  R  Q  F  Q  W  T  A  R  V  E  G  D  S  R  F  T  N  S  S  H  A  M
ACTCTCAGCCAGTACCTCGGCCGTGGGTCGCGTGTCGCACAACGCCGGTCATTCAGGGCATCAAGAA    2030
 T  L  S  Q  Y  L  G  R  G  V  S  R  G  R  A  T  I  T  Q  G  L  V
CCACCGTGGCTGAGCACCCGTACCTCCACAACGCCGGCGACAAGGAGGCCGTCATTCAGGGCATCAAGAA  2100
 T  T  V  A  E  H  P  Y  L  H  N  A  G  D  K  E  A  V  I  Q  G  I  K  N
CCTCATTGAGTCTCTTAACGTGATTCCCAACATCACTTGGGTCCTCCCTCCTGGTAGCACTGTCGAG    2170
 L  I  E  S  L  N  V  I  P  N  I  T  W  V  L  P  P  G  S  T  V  E
GAATACGTTGATTCGCTCCTCGTCGCGTCCGCTCGTCGTTCGAACCTCGACACCAAGGTCTACGGCACCGA  2240
 E  Y  V  D  S  L  L  V  S  A  S  A  R  R  S  N  H  W  M  G  T  A  K
TGGGTACTGATGATGGCCGCTACGGCCGTTCGATGCTTCCATCTTCCCTGGCATGTCGACCGGCAAGC   2310
 L  G  T  D  D  G  R  Y  G  G  T  S  V  V  D  L  D  T  K  V  Y  G  T  D
TAACCTGTTCGTTGTGATGGCTTCCATCTTCCCTGGCATGTCGACCGGCAACCCGTCCGCTATGATCGTG  2380
 N  L  F  V  D  A  S  I  F  P  G  M  S  T  G  N  P  S  A  M  I  V
ATTGCCGCTGAGCAGGCTGCGGAGCGCATTCTTAAGCTGAGGAAGTAAGAAGGGGAGAGGATGGAGGG   2450
 I  A  E  Q  A  A  E  R  I  L  K  L  R  K  .
ATGACATTGAGGAAAAATAGGGTTATGAGTTGATGAGTTATGGGCGAATGTGTCAGCCAGTGTACTTGACT  2520
TATTACCTGAGTTAAACAACGACGTGCTTGATGTGTTAAAAAAAAAACTTT  2576
```

NUCLEIC ACIDS ENCODING POLYPEPTIDES HAVING CELLOBIOSE DEHYDROGENASE ACTIVITY

BACKGROUND OF THE INVENTION

1. Field of the Invention

The present invention relates to isolated nucleic acid sequences encoding polypeptides having cellobiose dehydrogenase activity. The invention also relates to nucleic acid constructs, vectors, and host cells comprising the nucleic acid sequences as well as recombinant methods for producing the polypeptides.

2. Description of the Related Art

Cellobiose-oxidizing enzymes were first described in the extracellular enzyme system of the white-rot fungus *Phanerochaete chrysosporium* (Westermark and Eriksson, 1974, *Acta Chem. Scand. Ser. B* 28: 204–208; Westermark and Eriksson, 1974, *Acta Chem. Scand. Ser. B* 28: 209–214; Ayers et al., 1978, *European Journal of Biochemistry* 90: 171–181). The cellobiose-oxidizing enzymes from this fungus have been identified: one is a flavoprotein called cellobiose:quinone oxidoreductase (E.C. 1.1.5.1) suggested to be involved in lignin degradation, and the other is a haemoflavoprotein called cellobiose dehydrogenase (E.C. 1.1.99.18) proposed to be preferentially involved in cellulose degradation.

Cellobiose dehydrogenases have also been found in the brown-rot fungus *Coniophora putena* (Schmidhalter and Canevascini, 1992, *Applied Microbiology Biotechnology* 37: 431–436) and soft-rot fungi such as *Monilia* sp. (Dekker, 1980, Journal of General Microbiology 120: 309–316), *Chaetomium cellulolyticum* (Fähnrich and Irrgang, *Biotechnology Letters* 4: 775–780), *Myceliophthora thermophila* (Coudray et al., 1982, *Biochemical Journal* 203: 277–284), *Sclerotium rolfsii* (Sadana and Patil, 1985, *Journal of General Microbiology* 131: 1917–1923), and *Humicola insolens* (Schou et al., 1998, *Biochemical Journal* 330: 565–571).

The cloning of the *Phanerochaete chrysosporium* cellobiose dehydrogenase gene has been disclosed (Raices et al., 1995, *FEBS Letters* 369: 233–238).

It is an object of the present invention to provide alternative isolated nucleic acid sequences encoding polypeptides having cellobiose dehydrogenase activity.

SUMMARY OF THE INVENTION

The present invention relates to isolated nucleic acid sequences encoding polypeptides having cellobiose dehydrogenase activity, selected from the group consisting of:

(a) a nucleic acid sequence encoding a polypeptide having an amino acid sequence which has at least 65% identity with amino acids 22 to 785 of SEQ ID NO:2;

(b) a nucleic acid sequence having at least 65% homology with nucleotides 135 to 2425 of SEQ ID NO:1;

(c) a nucleic acid sequence which hybridizes under low stringency conditions with (i) nucleotides 135 to 2425 of SEQ ID NO:1, (ii) the genomic sequence comprising nucleotides 135 to 2425 of SEQ ID NO:1, (iii) a subsequence of (i) or (ii) of at least 100 nucleotides, or (iv) a complementary strand of (i), (ii), or (iii);

(d) a nucleic acid sequence encoding a variant of the polypeptide having an amino acid sequence of SEQ ID NO:2 comprising a substitution, deletion, and/or insertion of one or more amino acids;

(e) an allelic variant of (a), (b), or (c);

(f) a subsequence of (a), (b), (c), or (e), wherein the subsequence encodes a polypeptide fragment which has cellobiose dehydrogenase activity; and (g) a nucleic acid sequence encoding a polypeptide having cellobiose dehydrogenase activity with a pH optimum at a pH of about 5–9, such as about pH 7, using DCPIP or benzoquinones as the electron acceptor, about pH 7–9 using cytochrome C as the electron acceptor; and about pH 9 using ferric cyanide as the electron acceptor; a temperature optimum of 55° C. at pH 9.5, a molecular weight of about 92 kD by SDS-PAGE; an isoelectric point of about 4–5; a relative activity of at least 70% at a pH of about 9 and a temperature of about 50° C.; and stability at a pH of 5–10.

The present invention also relates to nucleic acid constructs, vectors, and host cells comprising the nucleic acid sequences as well as recombinant methods for producing the polypeptides.

BRIEF DESCRIPTION OF THE FIGURES

FIGS. 3A, B, and C show the cDNA sequence and the deduced amino acid sequence of a *Humicola insolens* DSM 1800 cellobiose dehydrogenase (SEQ ID NOS:1 and 2, respectively).

DETAILED DESCRIPTION OF THE INVENTION

Figure 1:
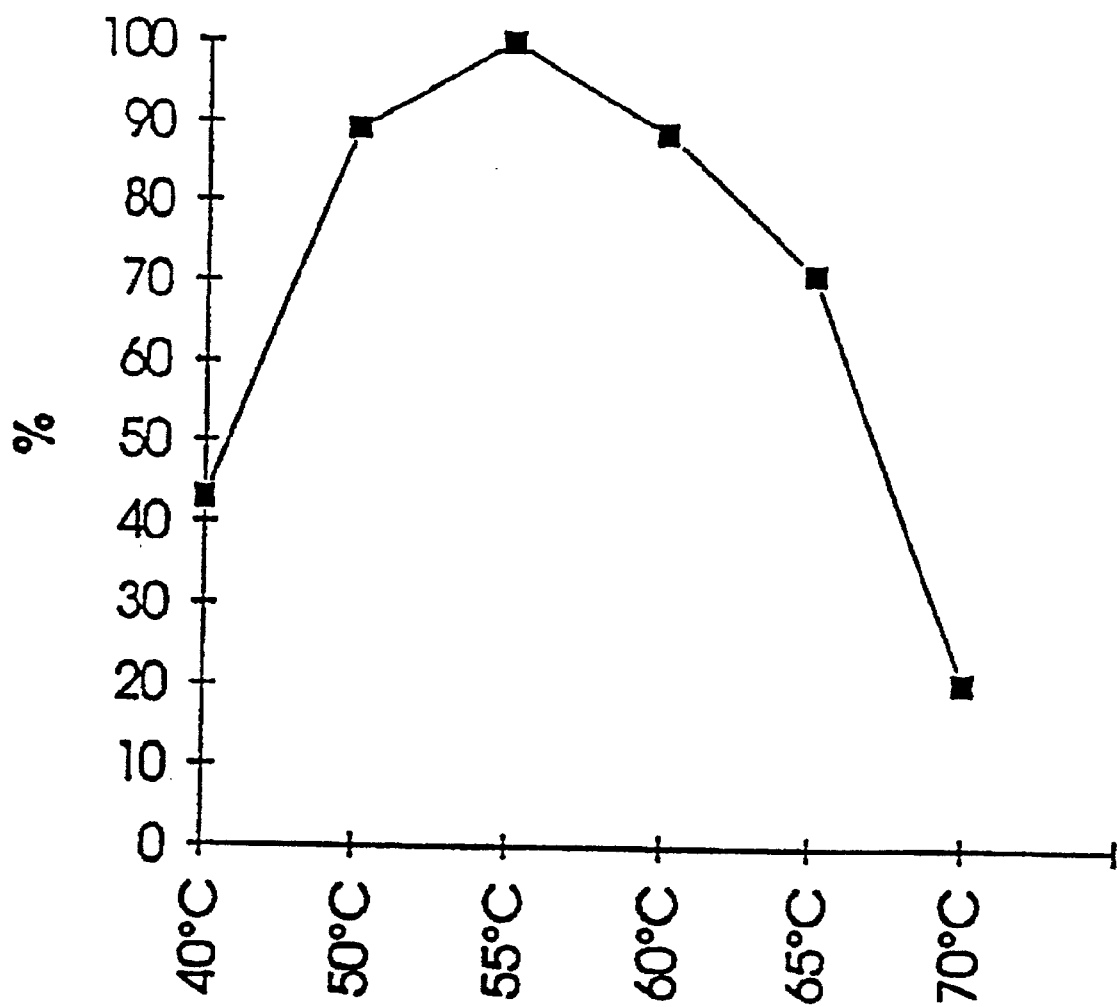
FIG. 1 shows the temperature activity profile of a *Humicola insolens* DSM 1800 cellobiose dehydrogenase in 0.1 M glycine pH 9.5.

Isolated Nucleic Acid Sequences Encoding Polypeptides Having Cellobiose Dehydrogenase Activity The term "cellobiose dehydrogenase activity" is defined herein as a cellobiose:(acceptor) oxidoreductase activity which catalyzes the conversion of cellobiose in the presence of an electron acceptor to cellobiono-1,5-lactone and a reduced acceptor. The natural substrate is cellobiose, but lactose, maltose, 4-methylumbelliferyl-beta-D-cellobioside, 4-beta-glucosylmannose, cello-oligosaccharides, cellodextrin, and xylobiose may also be substrates. The acceptor may be 2,6-dichlorophenolindophenol (DCPIP), phenol blue, cytochrome c, methylene blue, potassium ferricyanide, $Fe^{3+}$, 3,5-di-tert-butyl-1,2-benzoquinone, and p-benzoquinone. For purposes of the present invention, cellobiose dehydrogenase activity is determined according to the procedure described by Schou et al., 1998, supra, where a 450 μl solution of 100 μM DCPIP and 250 μM of cellobiose in 0.1 M sodium phosphate pH 7.5 buffer is mixed with 50 μl of the enzyme and the reduction of DCPIP is measured at 530 nm (40° C.). One unit of cellobiose dehydrogenase activity is defined as 1.0 μmole of cellobiose oxidized per minute at 40° C., pH 7.5.

The term "isolated nucleic acid sequence" as used herein refers to a nucleic acid sequence which is essentially free of other nucleic acid sequences, e.g., at least about 20% pure, preferably at least about 40% pure, more preferably at least about 60% pure, even more preferably at least about 80% pure, and most preferably at least about 90% pure as determined by agarose electrophoresis. For example, an isolated nucleic acid sequence can be obtained by standard cloning procedures used in genetic engineering to relocate the nucleic acid sequence from its natural location to a different site where it will be reproduced. The cloning procedures may involve excision and isolation of a desired nucleic acid fragment comprising the nucleic acid sequence encoding the polypeptide, insertion of the fragment into a vector molecule, and incorporation of the recombinant vector into a host cell where multiple copies or clones of the nucleic acid sequence will be replicated. The nucleic acid sequence may be of genomic, cDNA, RNA, semisynthetic, synthetic origin, or any combinations thereof.

In a first embodiment, the present invention relates to isolated nucleic acid sequences encoding polypeptides having an amino acid sequence which has a degree of identity to amino acids 22 to 785 of SEQ ID NO:2 (i.e., the mature polypeptide) of at least about 65%, preferably at least about 70%, more preferably at least about 80%, even more preferably at least about 90%, most preferably at least about 95%, and even most preferably at least about 97%, which have cellobiose dehydrogenase activity (hereinafter "homologous polypeptides"). In a preferred embodiment, the homologous polypeptides have an amino acid sequence which differs by five amino acids, preferably by four amino acids, more preferably by three amino acids, even more preferably by two amino acids, and most preferably by one amino acid from amino acids 22 to 785 of SEQ ID NO:2. For purposes of the present invention, the degree of identity between two amino acid sequences is determined by the Clustal method (Higgins, 1989, *CABIOS* 5: 151–153) using the LASERGENE™ MEGALIGN™ software (DNASTAR, Inc., Madison, Wis.) with an identity table and the following multiple alignment parameters: Gap penalty of 10, and gap length penalty of 10. Pairwise alignment parameters were Ktuple=1, gap penalty=3, windows=5, and diagonals=5.

Preferably, the nucleic acid sequences of the present invention encode polypeptides that comprise the amino acid sequence of SEQ ID NO:2 or an allelic variant thereof; or a fragment thereof that has cellobiose dehydrogenase activity. In a more preferred embodiment, the nucleic acid sequence of the present invention encodes a polypeptide that comprises the amino acid sequence of SEQ ID NO:2. In another preferred embodiment, the nucleic acid sequence of the present invention encodes a polypeptide that comprises amino acids 22 to 785 of SEQ ID NO:2 or an allelic variant thereof; or a fragment thereof that has cellobiose dehydrogenase activity. In another preferred embodiment, the nucleic acid sequence of the present invention encodes a polypeptide that comprises amino acids 22 to 785 of SEQ ID NO:2. In another preferred embodiment, the nucleic acid sequence of the present invention encodes a polypeptide that consists of the amino acid sequence of SEQ ID NO:2 or an allelic variant thereof; or a fragment thereof, wherein the polypeptide fragment has cellobiose dehydrogenase activity. In another preferred embodiment, the nucleic acid sequence of the present invention encodes a polypeptide that consists of the amino acid sequence of SEQ ID NO:2. In another preferred embodiment, the nucleic acid sequence of the present invention encodes a polypeptide that consists of amino acids 22 to 785 of SEQ ID NO:2 or an allelic variant thereof; or a fragment thereof that has cellobiose dehydrogenase activity. In another preferred embodiment, the nucleic acid sequence of the present invention encodes a polypeptide that consists of amino acids 22 to 785 of SEQ ID NO:2.

The present invention also encompasses nucleic acid sequences that encode a polypeptide having the amino acid sequence of SEQ ID NO:2, which differ from SEQ ID NO:1 by virtue of the degeneracy of the genetic code. The present invention also relates to subsequences of SEQ ID NO:1 which encode fragments of SEQ ID NO:2 which have cellobiose dehydrogenase activity.

A subsequence of SEQ ID NO:1 is a nucleic acid sequence encompassed by SEQ ID NO:1 except that one or more nucleotides from the 5' and/or 3' end have been deleted. Preferably, a subsequence contains at least 2010 nucleotides, more preferably at least 2100 nucleotides, and most preferably at least 2190 nucleotides. A fragment of SEQ ID NO:2 is a polypeptide having one or more amino acids deleted from the amino and/or carboxy terminus of this amino acid sequence. Preferably, a fragment contains at least 670 amino acid residues, more preferably at least 700 amino acid residues, and most preferably at least 730 amino acid residues.

An allelic variant denotes any of two or more alternative forms of a gene occupying the same chomosomal locus. Allelic variation arises naturally through mutation, and may result in polymorphism within populations. Gene mutations can be silent (no change in the encoded polypeptide) or may encode polypeptides having altered amino acid sequences. The allelic variant of a polypeptide is a polypeptide encoded by an allelic variant of a gene.

In a second embodiment, the present invention relates to isolated nucleic acid sequences which have a degree of homology to the mature polypeptide coding sequence of SEQ ID NO:1 (i.e., nucleotides 135 to 2425) of at least about 65%, preferably at least about 70%, preferably at least about 80%, more preferably at least about 90%, even more preferably at least about 95%, and most preferably at least about 97% homology, which encode an active polypeptide; or allelic variants and subsequences of SEQ ID NO:1 which encode polypeptide fragments which have cellobiose dehydrogenase activity. For purposes of the present invention, the degree of homology between two nucleic acid sequences is determined by the Wilbur-Lipman method (Wilbur and Lipman, 1983, *Proceedings of the National Academy of Science USA* 80: 726–730) using the LASERGENE™ MEGALIGN™ software (DNASTAR, Inc., Madison, Wis.) with an identity table and the following multiple alignment parameters: Gap penalty of 10, and gap length penalty of 10. Pairwise alignment parameters were Ktuple=3, gap penalty=3, and windows=20.

In a third embodiment, the present invention relates to isolated nucleic acid sequences encoding polypeptides having cellobiose dehydrogenase activity which hybridize under very low stringency conditions, preferably low stringency conditions, more preferably medium stringency conditions, more preferably medium-high stringency conditions, even more preferably high stringency conditions, and most preferably very high stringency conditions with a nucleic acid probe which hybridizes under the same conditions with (i) nucleotides 135 to 2425 of SEQ ID NO:1, (ii) the genomic sequence comprising nucleotides 135 to 2425 of SEQ ID NO:1, (iii) a subsequence of (i) or (ii), or (iv) a complementary strand of (i), (ii), or (iii) (J. Sambrook, E. F. Fritsch, and T. Maniatus, 1989, *Molecular Cloning, A Laboratory Manual,* 2d edition, Cold Spring Harbor, N.Y). The subsequence of SEQ ID NO:1 may be at least 100 nucleotides or preferably at least 200 nucleotides. Moreover, the subsequence may encode a polypeptide fragment which has cellobiose dehydrogenase activity.

The nucleic acid sequence of SEQ ID NO:1 or a subsequence thereof, as well as the amino acid sequence of SEQ ID NO:2 or a fragment thereof, may be used to design a nucleic acid probe to identify and clone DNA encoding polypeptides having cellobiose dehydrogenase activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 15, preferably at least 25, and more preferably at least 35 nucleotides in length. Longer probes can also be used. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

Thus, a genomic DNA or cDNA library prepared from such other organisms may be screened for DNA which hybridizes with the probes described above and which encodes a polypeptide having cellobiose dehydrogenase activity. Genomic or other DNA from such other organisms may be separated by agarose or polyacrylamide gel electrophoresis, or other separation techniques. DNA from the libraries or the separated DNA may be transferred to and immobilized on nitrocellulose or other suitable carrier material. In order to identify a clone or DNA which is homologous with SEQ ID NO:1 or a subsequence thereof, the carrier material is used in a Southern blot. For purposes of the present invention, hybridization indicates that the nucleic acid sequence hybridizes to a labeled nucleic acid probe corresponding to the nucleic acid sequence shown in SEQ ID NO:1, its complementary strand, or a subsequence thereof, under very low to very high stringency conditions. Molecules to which the nucleic acid probe hybridizes under these conditions are detected using X-ray film.

In a preferred embodiment, the nucleic acid probe is a nucleic acid sequence which encodes the polypeptide of SEQ ID NO:2, or a subsequence thereof. In another preferred embodiment, the nucleic acid probe is SEQ ID NO:1. In another preferred embodiment, the nucleic acid probe is nucleotides 135 to 2425 of SEQ ID NO:1, which encode a mature polypeptide having cellobiose dehydrogenase activity. In another preferred embodiment, the nucleic acid probe is the nucleic acid sequence contained in plasmid pEJG44 which is contained in *Escherichia coli* NRRL B-30065, wherein the nucleic acid sequence encodes a polypeptide having cellobiose dehydrogenase activity. In another preferred embodiment, the nucleic acid probe is the mature polypeptide coding region contained in plasmid pEJG44 which is contained in *Escherichia coli* NRRL B-30065.

For long probes of at least 100 nucleotides in length, very low to very high stringency conditions are defined as prehybridization and hybridization at 42° C. in 5× SSPE, 0.3% SDS, 200 μg/ml sheared and denatured salmon sperm DNA, and either 25% formamide for very low and low stringencies, 35% formamide for medium and medium-high stringencies, or 50% formamide for high and very high stringencies, following standard Southern blotting procedures.

For long probes of at least 100 nucleotides in length, the carrier material is finally washed three times each for 15 minutes using 2×SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency).

For short probes which are about 15 nucleotides to about 70 nucleotides in length, stringency conditions are defined as prehybridization, hybridization, and washing post-hybridization at 5° C. to 10° C. below the calculated $T_m$ using the calculation according to Bolton and McCarthy (1962, *Proceedings of the National Academy of Sciences USA* 48:1390) in 0.9 M NaCl, 0.09 M Tris-HCl pH 7.6, 6 mM EDTA, 0.5% NP-40, 1× Denhardt's solution, 1 mM sodium pyrophosphate, 1 mM sodium monobasic phosphate, 0.1 mM ATP, and 0.2 mg of yeast RNA per ml following standard Southern blotting procedures.

For short probes which are about 15 nucleotides to about 70 nucleotides in length, the carrier material is washed once in 6× SCC plus 0.1% SDS for 15 minutes and twice each for 15 minutes using 6× SSC at 5° C. to 10° C. below the calculated $T_m$.

The present invention also relates to isolated nucleic acid sequences produced by (a) hybridizing a DNA under very low, low, medium, medium-high, high, or very high stringency conditions with (i) nucleotides 135 to 2425 of SEQ ID NO:1, (ii) the genomic sequence comprising nucleotides 135 to 2425 of SEQ ID NO:1, (iii) a subsequence of (i) or (ii), or (iv) a complementary strand of (i), (ii), or (iii); and (b) isolating the nucleic acid sequence. The subsequence is preferably a sequence of at least 100 nucleotides such as a sequence which encodes a polypeptide fragment which has cellobiose dehydrogenase activity.

In a fourth embodiment, the present invention relates to isolated nucleic acid sequences which encode variants of the polypeptide having an amino acid sequence of SEQ ID NO:2 comprising a substitution, deletion, and/or insertion of one or more amino acids.

The amino acid sequences of the variant polypeptides may differ from the amino acid sequence of SEQ ID NO:2 or the mature polypeptide thereof by an insertion or deletion of one or more amino acid residues and/or the substitution of one or more amino acid residues by different amino acid residues. Preferably, amino acid changes are of a minor nature, that is conservative amino acid substitutions that do not significantly affect the folding and/or activity of the protein; small deletions, typically of one to about 30 amino acids; small amino- or carboxyl-terminal extensions, such as an amino-terminal methionine residue; a small linker peptide of up to about 20–25 residues; or a small extension that facilitates purification by changing net charge or another function, such as a poly-histidine tract, an antigenic epitope or a binding domain.

Examples of conservative substitutions are within the group of basic amino acids (such as arginine, lysine and histidine), acidic amino acids (such as glutamic acid and aspartic acid), polar amino acids (such as glutamine and asparagine), hydrophobic amino acids (such as leucine, isoleucine and valine), aromatic amino acids (such as phenylalanine, tryptophan and tyrosine), and small amino acids (such as glycine, alanine, serine, threonine and methionine). Amino acid substitutions which do not generally alter the specific activity are known in the art and are described, for example, by H. Neurath and R. L. Hill, 1979, *In, The Proteins,* Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Ile, Ala/Glu, and Asp/Gly as well as these in reverse.

Modification of a nucleic acid sequence of the present invention may be necessary for the synthesis of variant polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermostability, pH optimum, or the like. The variant sequence may be constructed on the basis of the nucleic acid sequence presented as the polypeptide encoding part of SEQ ID NO:1, e.g., a subsequence thereof, and/or by introduction of nucleotide substitutions which do not give rise to another amino acid sequence of the polypeptide encoded by the nucleic acid sequence, but which corresponds to the codon usage of the host organism intended for production of the enzyme, or by introduction of nucleotide substitutions which may give rise to a different amino acid sequence. For a general description of nucleotide substitution, see, e.g., Ford et al., 1991, *Protein Expression and Purification* 2: 95–107.

It will be apparent to those skilled in the art that such substitutions can be made outside the regions critical to the function of the molecule and still result in an active polypeptide. Amino acid residues essential to the activity of the polypeptide encoded by the isolated nucleic acid sequence of the invention, and therefore preferably not subject to substitution, may be identified according to procedures known in the art, such as site-directed mutagenesis or alanine-scanning mutagenesis (see, e.g., Cunningham and Wells, 1989, *Science* 244: 1081–1085). In the latter technique, mutations are introduced at every positively charged residue in the molecule, and the resultant mutant molecules are tested for cellobiose dehydrogenase activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labelling (see, e.g., de Vos et al., 1992, *Science* 255: 306–312; Smith et al., 1992, *Journal of Molecular Biology* 224: 899–904; Wlodaver et al., 1992, *FEBS Letters* 309: 59–64).

In a fifth embodiment, the present invention relates to isolated nucleic acid sequences encoding polypeptides with cellobiose dehydrogenase activity having the following physicochemical properties: A pH optimum at a pH of about 5–9, such as about pH 7 using DCPIP or benzoquinones as the electron acceptor, about pH 7–9 using cytochrome C as the electron acceptor; and about pH 9 using ferric cyanide as the electron acceptor; a temperature optimum of 55° C. at pH 9.5, a molecular weight of about 92 kD by SDS-PAGE; an isoelectric point of about 4–5; a relative activity of at least 70% at a pH of about 9 and a temperature of about 50° C.; and stability at a pH of 5–10 (see, for example WO 94/01538).

The polypeptides encoded by the isolated nucleic acid sequences of the present invention have at least 20%, preferably at least 40%, more preferably at least 60%, even more preferably at least 80%, even more preferably at least 90%, and most preferably at least 100% of the cellobiose dehydrogenase activity of the mature polypeptide of SEQ ID NO:2.

The nucleic acid sequences of the present invention may be obtained from microorganisms of any genus. For purposes of the present invention, the term "obtained from" as used herein in connection with a given source shall mean that the polypeptide encoded by the nucleic acid sequence is produced by the source or by a cell in which the nucleic acid sequence from the source has been inserted. In a preferred embodiment, the polypeptide encoded by a nucleic acid sequence of the present invention is secreted extracellularly.

The nucleic acid sequences may be obtained from a bacterial source. For example, these polypeptides may be obtained from a gram positive bacterium such as a Bacillus strain, e.g., *Bacillus alkalophilus, Bacillus amyloliquefaciens, Bacillus brevis, Bacillus circulans, Bacillus coagulans, Bacillus lautus, Bacillus lentus, Bacillus licheniformis, Bacillus megaterium, Bacillus stearothermophilus, Bacillus subtilis,* or *Bacillus thuringiensis;* or a Streptomyces strain, e.g., *Streptomyces lividans* or *Streptomyces murinus;* or from a gram negative bacterium, e.g., *E. coli* or Pseudomonas sp.

The nucleic acid sequences may be obtained from a fungal source, and more preferably from a yeast strain such as a Candida, Hansenula, Kluyveromyces, Pichia, Saccharomyces, Schizosaccharomyces, or Yarrowia strain; or more preferably from a filamentous fungal strain such as an Acremonium, Aspergillus, Aureobasidium, Cryptococcus, Filibasidium, Fusarium, Humicola, Magnaporthe, Mucor, Myceliophthora, Neocallimastix, Neurospora, Paecilomyces, Penicillium, Piromyces, Schizophyllum, Talaromyces, Thermoascus, Thielavia, Tolypocladium, or Trichoderma strain.

In a preferred embodiment, the nucleic acid sequences are obtained from a *Saccharomyces carlsbergensis, Saccharomyces cerevisiae, Saccharomyces diastaticus, Saccharomyces douglasii, Saccharomyces kluyveri, Saccharomyces norbensis,* or *Saccharomyces oviformis* strain.

In another preferred embodiment, the nucleic acid sequences are obtained from an *Aspergillus aculeatus, Aspergillus awamori, Aspergillus foetidus, Aspergillus japonicus, Aspergillus nidulans, Aspergillus niger, Aspergillus oryzae, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Mucor miehei, Myceliophthora thermophila, Neurospora crassa, Penicillium purpurogenum, Trichoderma harzianum, Trichoderma koningii, Trichoderma longibrachiatum, Trichoderma reesei,* or *Trichoderma viride* strain.

In another preferred embodiment, the nucleic acid sequences are obtained from a *Humicola alopallonella, Humicola asteroides, Humicola brevis, Humicola brevispora, Humicola brunnea, Humicola dimorphospora, Humicola fuscoatra, Humicola grisea, Humicola hyalothermophila, Humicola insolens, Humicola lanuginosa, Humicola minima, Humicola nigrescens, Humicola parvispora, Humicola stellata, Humicola tainanensis, Humicola veronae,* or *Humicola zollerniae* strain.

In a more preferred embodiment, the nucleic acid sequences are obtained from *Humicola insolens,* and most preferably from *Humicola insolens* DSM 1800, e.g., the nucleic acid sequence set forth in SEQ ID NO:1. In another more preferred embodiment, the nucleic acid sequence is the sequence contained in plasmid pEJG44 which is contained in *Escherichia coli* NRRL B-30065. In another preferred embodiment, the nucleic acid sequence is nucleotides 135 to 2425 of SEQ ID NO:1.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents. For example, the polypeptides may be obtained from microorganisms which are taxonomic equivalents of Humicola as defined by S. C. Jong, J. M. Birmingham, and G. Ma in ATCC *Names of Industrial Fungi,* American Type Culture Collection, Rockville, Md., 1994, or M. B. Ellis in *Dematiaceous Hyphomycetes*, Commonwealth Mycological Institute, Surrey, England, 1971, regardless of the species name by which they are known.

Strains of these species are readily accessible to the public in a number of culture collections, such as the American Type Culture Collection (ATCC), Deutsche Sammlung von Mikroorganismen und Zellkulturen GmbH (DSM), Centraalbureau Voor Schimmelcultures (CBS), and Agricultural Research Service Patent Culture Collection, Northern Regional Research Center (NRRL).

Furthermore, such nucleic acid sequences may be identified and obtained from other sources including microorganisms isolated from nature (e.g., soil, composts, water, etc.) using the above-mentioned probes. Techniques for isolating microorganisms from natural habitats are well known in the art. The nucleic acid sequence may then be derived by similarly screening a genomic or cDNA library of another microorganism. Once a nucleic acid sequence encoding a polypeptide has been detected with the probe(s), the sequence may be isolated or cloned by utilizing techniques which are known to those of ordinary skill in the art (see, e.g., Sambrook et al., 1989, supra).

The present invention also relates to mutant nucleic acid sequences comprising at least one mutation in the mature polypeptide coding sequence of SEQ ID NO:1, in which the mutant nucleic acid sequence encodes a polypeptide which consists of amino acids 22 to 785 of SEQ ID NO:2.

The techniques used to isolate or clone a nucleic acid sequence encoding a polypeptide are known in the art and include isolation from genomic DNA, preparation from cDNA, or a combination thereof. The cloning of the nucleic acid sequences of the present invention from such genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application,* Academic Press, New York. Other nucleic acid amplification procedures such as ligase chain reaction (LCR), ligated activated transcription (LAT) and nucleic acid sequence-based amplification (NASBA) may be used. The nucleic acid sequence may be cloned from a strain of Humicola, or another or related organism and thus, for example, may be an allelic or species variant of the polypeptide encoding region of the nucleic acid sequence.

A nucleic acid sequence of the present invention may also encode fused polypeptides or cleavable fusion polypeptides in which another polypeptide is fused at the N-terminus or the C-terminus of the polypeptide or fragment thereof. A fused polypeptide is produced by fusing a nucleic acid sequence (or a portion thereof) encoding another polypeptide to a nucleic acid sequence (or a portion thereof) of the present invention. Techniques for producing fusion polypeptides are known in the art, and include ligating the coding sequences encoding the polypeptides so that they are in frame and that expression of the fused polypeptide is under control of the same promoter(s) and terminator.

Methods for Producing Mutant Nucleic Acid Sequences

The present invention further relates to methods for producing a mutant nucleic acid sequence, comprising introducing at least one mutation into the mature polypeptide coding sequence of SEQ ID NO:1 or a subsequence thereof, wherein the mutant nucleic acid sequence encodes a polypeptide which consists of amino acids 22 to 785 of SEQ ID NO:2 or a fragment thereof which has cellobiose dehydrogenase activity.

The introduction of a mutation into the nucleic acid sequence to exchange one nucleotide for another nucleotide may be accomplished by site-directed mutagenesis using any of the methods known in the art. Particularly useful is the procedure which utilizes a supercoiled, double stranded DNA vector with an insert of interest and two synthetic primers containing the desired mutation. The oligonucleotide primers, each complementary to opposite strands of the vector, extend during temperature cycling by means of Pfu DNA polymerase. On incorporation of the primers, a mutated plasmid containing staggered nicks is generated. Following temperature cycling, the product is treated with DpnI which is specific for methylated and hemimethylated DNA to digest the parental DNA template and to select for mutation-containing synthesized DNA. Other procedures known in the art may also be used.

Nucleic Acid Constructs

The present invention also relates to nucleic acid constructs comprising a nucleic acid sequence of the present invention operably linked to one or more control sequences which direct the expression of the coding sequence in a suitable host cell under conditions compatible with the control sequences. Expression will be understood to include any step involved in the production of the polypeptide including, but not limited to, transcription, post-transcriptional modification, translation, post-translational modification, and secretion.

"Nucleic acid construct" is defined herein as a nucleic acid molecule, either single- or double-stranded, which is isolated from a naturally occurring gene or which has been modified to contain segments of nucleic acid which are combined and juxtaposed in a manner which would not otherwise exist in nature. The term nucleic acid construct is synonymous with the term expression cassette when the nucleic acid construct contains all the control sequences required for expression of a coding sequence of the present invention. The term "coding sequence" is defined herein as a nucleic acid sequence which directly specifies the amino acid sequence of its protein product. The boundaries of the coding sequence are generally determined by a ribosome binding site (prokaryotes) or by the ATG start codon (eukaryotes) located just upstream of the open reading frame at the 5' end of the mRNA and a transcription terminator sequence located just downstream of the open reading frame at the 3' end of the mRNA. A coding sequence can include, but is not limited to, DNA, cDNA, and recombinant nucleic acid sequences.

An isolated nucleic acid sequence encoding a polypeptide of the present invention may be manipulated in a variety of ways to provide for expression of the polypeptide. Manipulation of the nucleic acid sequence prior to its insertion into a vector may be desirable or necessary depending on the expression vector. The techniques for modifying nucleic acid sequences utilizing recombinant DNA methods are well known in the art.

The term "control sequences" is defined herein to include all components which are necessary or advantageous for the expression of a polypeptide encoded by a nucleic acid sequence of the present invention. Each control sequence may be native or foreign to the nucleic acid sequence encoding the polypeptide. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleic acid sequence encoding a polypeptide. The term "operably linked" is defined herein as a configuration in which a control sequence is appropriately placed at a position relative to the coding sequence of the DNA sequence such that the control sequence directs the expression of a polypeptide.

The control sequence may be an appropriate promoter sequence, a nucleic acid sequence which is recognized by a host cell for expression of the nucleic acid sequence. The promoter sequence contains transcriptional control sequences which mediate the expression of the polypeptide. The promoter may be any nucleic acid sequence which shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, *Streptomyces coelicolor* agarase gene (dagA), *Bacillus subtilis* levansucrase gene (sacB), *Bacillus subtilis* alpha-amylase gene (amyE), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (Villa-Kamaroff et al., 1978, *Proceedings of the National Academy of Sciences USA* 75: 3727–3731), as well as the tac promoter (DeBoer et al., 1983, *Proceedings of the National Academy of Sciences USA* 80: 21–25). Further promoters are described in "Useful proteins from recombinant bacteria" in *Scientific American*, 1980, 242: 74–94; and in Sambrook et al., 1989, supra.

Examples of suitable promoters for directing the transcription of the nucleic acid constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium oxysporum* trypsin-like protease (WO 96/00787), as well as the NA2-tpi promoter (a hybrid of the promoters from the genes for *Aspergillus niger* neutral alpha-amylase and *Aspergillus oryzae* triose phosphate isomerase); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH2/GAP), and *Saccharomyces cerevisiae* 3-phosphoglycerate kinase. Other useful promoters for yeast host cells are described by Romanos et al., 1992, *Yeast* 8: 423–488.

The control sequence may also be a suitable transcription terminator sequence, a sequence recognized by a host cell to terminate transcription. The terminator sequence is operably linked to the 3' terminus of the nucleic acid sequence encoding the polypeptide. Any terminator which is functional in the host cell of choice may be used in the present invention.

Preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA which is important for translation by the host cell. The leader sequence is operably linked to the 5' terminus of the nucleic acid sequence encoding the polypeptide. Any leader sequence that is functional in the host cell of choice may be used in the present invention.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence which is operably linked to the 3' terminus of the nucleic acid sequence and which, when transcribed, is recognized by the host cell as a signal to add polyadenosine residues to transcribed mRNA. Any polyadenylation sequence which is functional in the host cell of choice may be used in the present invention.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Molecular Cellular Biology* 15: 5983–5990.

The control sequence may also be a signal peptide coding region that codes for an amino acid sequence linked to the amino terminus of a polypeptide and directs the encoded polypeptide into the cell's secretory pathway. The 5' end of the coding sequence of the nucleic acid sequence may inherently contain a signal peptide coding region naturally linked in translation reading frame with the segment of the coding region which encodes the secreted polypeptide. Alternatively, the 5' end of the coding sequence may contain a signal peptide coding region which is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the polypeptide. However, any signal peptide coding region which directs the expressed polypeptide into the secretory pathway of a host cell of choice may be used in the present invention.

Effective signal peptide coding regions for bacterial host cells are the signal peptide coding regions obtained from the genes for Bacillus NCIB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109–137.

Effective signal peptide coding regions for filamentous fungal host cells are the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, and *Humicola lanuginosa* lipase.

In a preferred embodiment, the signal peptide coding region is nucleotides 71 to 134 of SEQ ID NO:1 which encode amino acids 1 to 21 of SEQ ID NO:2.

Useful signal peptides for yeast host cells are obtained from the genes for *Saccharomyces cerevisiae* alpha-factor and *Saccharomyces cerevisiae* invertase. Other useful signal peptide coding regions are described by Romanos et al., 1992, supra.

The control sequence may also be a propeptide coding region that codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* laccase (WO 95/33836).

Where both signal peptide and propeptide regions are present at the amino terminus of a polypeptide, the propeptide region is positioned next to the amino terminus of the polypeptide and the signal peptide region is positioned next to the amino terminus of the propeptide region.

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the TAKA alpha-amylase promoter, *Aspergillus niger* glucoamylase promoter, and the *Aspergillus oryzae* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleic acid sequence encoding the polypeptide would be operably linked with the regulatory sequence.

Expression Vectors

The present invention also relates to recombinant expression vectors comprising a nucleic acid sequence of the present invention, a promoter, and transcriptional and translational stop signals. The various nucleic acid and control sequences described above may be joined together to produce a recombinant expression vector which may include one or more convenient restriction sites to allow for insertion or substitution of the nucleic acid sequence encoding the polypeptide at such sites. Alternatively, the nucleic acid sequence of the present invention may be expressed by inserting the nucleic acid sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) which can be conveniently subjected to recombinant DNA procedures and can bring about the expression of the nucleic acid sequence. The choice of the vector will typically depend on the compatibility of the vector with the host cell into which the vector is to be introduced. The vectors may be linear or closed circular plasmids.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like. Examples of bacterial selectable markers are the dal genes from *Bacillus subtilis* or *Bacillus licheniformis,* or markers which confer antibiotic resistance such as ampicillin, kanamycin, chloramphenicol or tetracycline resistance. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hygB (hygromycin phosphotransferase), niaD (nitrate reductase), pyrG (orotidine-5'-phosphate decarboxylase), sC (sulfate adenyltransferase), trpC (anthranilate synthase), as well as equivalents thereof. Preferred for use in an Aspergillus cell are the amdS and pyrG genes of *Aspergillus nidulans* or *Aspergillus oryzae* and the bar gene of *Streptomyces hygroscopicus.*

The vectors of the present invention preferably contain an element(s) that permits stable integration of the vector into the host cell's genome or autonomous replication of the vector in the cell independent of the genome.

For integration into the host cell genome, the vector may rely on the nucleic acid sequence encoding the polypeptide or any other element of the vector for stable integration of the vector into the genome by homologous or nonhomologous recombination. Alternatively, the vector may contain additional nucleic acid sequences for directing integration by homologous recombination into the genome of the host cell. The additional nucleic acid sequences enable the vector to be integrated into the host cell genome at a precise location(s) in the chromosome(s). To increase the likelihood of integration at a precise location, the integrational elements should preferably contain a sufficient number of nucleic acids, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences. On the other hand, the vector may be integrated into the genome of the host cell by non-homologous recombination.

For autonomous replication, the vector may further comprise an origin of replication enabling the vector to replicate autonomously in the host cell in question. Examples of bacterial origins of replication are the origins of replication of plasmids pBR322, pUC19, pACYC177, and pACYC184 permitting replication in *E. coli,* and pUB110, pE194, pTA1060, and pAMβ1 permitting replication in Bacillus. Examples of origins of replication for use in a yeast host cell are the 2 micron origin of replication, ARS1, ARS4, the combination of ARS1 and CEN3, and the combination of ARS4 and CEN6. The origin of replication may be one having a mutation which makes its functioning temperature-sensitive in the host cell (see, e.g., Ehrlich, 1978, *Proceedings of the National Academy of Sciences USA* 75: 1433).

More than one copy of a nucleic acid sequence of the present invention may be inserted into the host cell to increase production of the gene product. An increase in the copy number of the nucleic acid sequence can be obtained by integrating at least one additional copy of the sequence into the host cell genome or by including an amplifiable selectable marker gene with the nucleic acid sequence where cells containing amplified copies of the selectable marker gene, and thereby additional copies of the nucleic acid sequence, can be selected for by cultivating the cells in the presence of the appropriate selectable agent.

The procedures used to ligate the elements described above to construct the recombinant expression vectors of the present invention are well known to one skilled in the, art (see, e.g., Sambrook et al., 1989, supra).

Host Cells

The present invention also relates to recombinant host cells, comprising a nucleic acid sequence of the invention, which are advantageously used in the recombinant production of the polypeptides. A vector comprising a nucleic acid sequence of the present invention is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be a unicellular microorganism, e.g., a prokaryote, or a non-unicellular microorganism, e.g., a eukaryote.

Useful unicellular cells are bacterial cells such as gram positive bacteria including, but not limited to, a Bacillus cell, e.g., *Bacillus alkalophilus, Bacillus amyloliquefaciens, Bacillus brevis, Bacillus circulans, Bacillus clausii, Bacillus coagulans, Bacillus lautus, Bacillus lentus, Bacillus licheniformis, Bacillus megaterium, Bacillus stearothermophilus, Bacillus subtilis,* and *Bacillus thuringiensis;* or a Streptomyces cell, e.g., *Streptomyces lividans* or *Streptomyces murinus,* or gram negative bacteria such as *E. coli* and Pseudomonas sp. In a preferred embodiment, the bacterial host cell is a *Bacillus lentus, Bacillus licheniformis, Bacillus stearothermophilus* or *Bacillus subtilis* cell. In another preferred embodiment, the Bacillus cell is an alkalophilic Bacillus.

The introduction of a vector into a bacterial host cell may, for instance, be effected by protoplast transformation (see, e.g., Chang and Cohen, 1979, *Molecular General Genetics* 168: 111–115), using competent cells (see, e.g., Young and Spizizin, 1961, *Journal of Bacteriology* 81: 823–829, or Dubnau and Davidoff-Abelson, 1971, *Journal of Molecular Biology* 56: 209–221), electroporation (see, e.g., Shigekawa and Dower, 1988, *Biotechniques* 6: 742–751), or conjugation (see, e.g., Koehler and Thorne, 1987, *Journal of Bacteriology* 169: 5771–5278).

The host cell may be a eukaryote, such as a mammalian, insect, plant, or fungal cell.

In a preferred embodiment, the host cell is a fungal cell. "Fungi" as used herein includes the phyla Ascomycota, Basidiomycota, Chytridiomycota, and Zygomycota (as defined by Hawksworth et al., In, *Ainsworth and Bisby's Dictionary of The Fungi,* 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a more preferred embodiment, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, *Soc. App. Bacteriol. Symposium Series* No. 9, 1980).

In an even more preferred embodiment, the yeast host cell is a Candida, Hansenula, Kluyveromyces, Pichia, Saccharomyces, Schizosaccharomyces, or Yarrowia cell.

In a most preferred embodiment, the yeast host cell is a *Saccharomyces carlsbergensis, Saccharomyces cerevisiae, Saccharomyces diastaticus, Saccharomyces douglasii, Saccharomyces kluyveri, Saccharomyces norbensis* or *Saccharomyces oviformis* cell. In another most preferred embodiment, the yeast host cell is a *Kluyveromyces lactis* cell. In another most preferred embodiment, the yeast host cell is a *Yarrowia lipolytica* cell.

In another more preferred embodiment, the fungal host cell is a filamentous fungal cell. "Filamentous fungi" include all filamentous forms of the subdivision Eumycota and Oomycota (as defined by Hawksworth et al., 1995, supra). The filamentous fungi are characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In an even more preferred embodiment, the filamentous fungal host cell is a cell of a species of, but not limited to, Acremonium, Aspergillus, Fusarium, Humicola, Mucor, Myceliophthora, Neurospora, Penicillium, Thielavia, Tolypocladium, or Trichoderma.

In a most preferred embodiment, the filamentous fungal host cell is an *Aspergillus awamori, Aspergillus foetidus, Aspergillus japonicus, Aspergillus nidulans, Aspergillus niger* or *Aspergillus oryzae* cell. In another most preferred embodiment, the filamentous fungal host cell is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides,* or

*Fusarium venenatum* cell. In an even most preferred embodiment, the filamentous fungal parent cell is a *Fusarium venenatum* (Nirenberg sp. nov.) cell. In another most preferred embodiment, the filamentous fungal host cell is a *Humicola insolens, Humicola lanuginosa, Mucor miehei, Myceliophthora thermophila, Neurospora crassa, Penicillium purpurogenum, Thielavia terrestris, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of Aspergillus host cells are described in EP 238 023 and Yelton et al., 1984, *Proceedings of the National Academy of Sciences USA* 81: 1470–1474. Suitable methods for transforming Fusarium species are described by Malardier et al., 1989, *Gene* 78: 147–156 and WO 96/00787. Yeast may be transformed using the procedures described by Becker and Guarente, In Abelson, J. N. and Simon, M. I., editors, *Guide to Yeast Genetics and Molecular Biology, Methods in Enzymology,* Volume 194, pp 182–187, Academic Press, Inc., New York; Ito et al., 1983, *Journal of Bacteriology* 153: 163; and Hinnen et al., 1978, *Proceedings of the National Academy of Sciences USA* 75: 1920.

Methods of Production

The present invention also relates to methods for producing a polypeptide having cellobiose dehydrogenase activity comprising (a) cultivating a host cell under conditions suitable for production of the polypeptide; and (b) recovering the polypeptide.

The present invention also relates to methods for producing a polypeptide having cellobiose dehydrogenase activity comprising (a) cultivating a host cell under conditions conducive for production of the polypeptide, wherein the host cell comprises a mutant nucleic acid sequence having at least one mutation in the mature polypeptide coding region of SEQ ID NO:1, wherein the mutant nucleic acid sequence encodes a polypeptide which consists of amino acids 22 to 785 of SEQ ID NO:2, and (b) recovering the polypeptide.

In the production methods of the present invention, the cells are cultivated in a nutrient medium suitable for production of the polypeptide using methods known in the art. For example, the cell may be cultivated by shake flask cultivation, small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptides may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide as described herein.

The resulting polypeptide may be recovered by methods known in the art. For example, the polypeptide may be recovered from the nutrient medium by conventional procedures including, but not limited to, centrifugation, filtration, extraction, spray-drying, evaporation, or precipitation.

The polypeptides may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification,* J.-C. Janson and Lars Ryden, editors, VCH Publishers, New York, 1989).

Plants

The present invention also relates to a transgenic plant, plant part, or plant cell which has been transformed with a nucleic acid sequence encoding a polypeptide having cellobiose dehydrogenase activity of the present invention so as to express and produce the polypeptide in recoverable quantities. The polypeptide may be recovered from the plant or plant part. Alternatively, the plant or plant part containing the recombinant polypeptide may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, Poa), forage grass such as festuca, lolium, temperate grass, such as Agrostis, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana.*

Examples of plant parts are stem, callus, leaves, root, fruits, seeds, and tubers. Also specific plant tissues, such as chloroplast, apoplast, mitochondria, vacuole, peroxisomes, and cytoplasm are considered to be a plant part. Furthermore, any plant cell, whatever the tissue origin, is considered to be a plant part.

Also included within the scope of the present invention are the progeny of such plants, plant parts and plant cells.

The transgenic plant or plant cell expressing a polypeptide of the present invention may be constructed in accordance with methods known in the art. Briefly, the plant or plant cell is constructed by incorporating one or more expression constructs encoding a polypeptide of the present invention into the plant host genome and propagating the resulting modified plant or plant cell into a transgenic plant or plant cell.

Conveniently, the expression construct is a nucleic acid construct which comprises a nucleic acid sequence encoding a polypeptide of the present invention operably linked with appropriate regulatory sequences required for expression of the nucleic acid sequence in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences is determined, for example, on the basis of when, where, and how the polypeptide is desired to be expressed.

For instance, the expression of the gene encoding a polypeptide of the present invention may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV promoter may be used (Franck et al., 1980, *Cell* 21: 285–294). Organ-specific promoters may be, for example, a promoter from storage sink tissues such as seeds, potato tubers, and fruits (Edwards & Coruzzi, 1990, *Ann. Rev. Genet.* 24: 275–303), or from metabolic sink tissues such as meristems (Ito et al., 1994, *Plant Mol. Biol.* 24: 863–878), a seed specific promoter such as the glutelin, prolamin, globulin, or albumin promoter from rice (Wu et al., 1998, *Plant and Cell Physiology* 39: 885–889) a *Vicia faba* promoter from the legumin B4 and the unknown seed protein gene from *Vicia faba* (Conrad et al., 1998, *Journal of Plant Physiology* 152: 708–711), a promoter from a seed oil body protein (Chen et al., 1998, Plant and Cell Physiology 39: 935–941), the storage protein napA promoter from *Brassica napus,* or any other seed specific promoter known in the art, e.g., as described in WO 91/14772. Furthermore, the promoter may be a leaf specific promoter such as the rbcs promoter from rice or tomato (Kyozuka et al., 1993, *Plant Physiology* 102: 991–1000), the chlorella virus adenine methyltransferase gene promoter (Mitra and Higgins, 1994, *Plant Molecular Biology* 26: 85–93) or the aldP gene promoter from rice (Kagaya et al., 1995, *Molecular and General Genetics* 248: 668–674), or a wound inducible promoter such as the potato pin2 promoter (Xu et al., 1993, *Plant Molecular Biology* 22: 573–588).

A promoter enhancer element may also be used to achieve higher expression of the enzyme in the plant. For instance, the promoter enhancer element may be an intron which is placed between the promoter and the nucleotide sequence encoding a polypeptide of the present invention. For instance, Xu et al., 1993, supra disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including Agrobacterium-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

Presently, *Agrobacterium tumefaciens*-mediated gene transfer is the method of choice for generating transgenic dicots (for a review, see Hooykas and Schilperoort, 1992, *Plant Molecular Biology* 19: 15–38). However it can also be used for transforming monocots, although other transformation methods are generally preferred for these plants. Presently, the method of choice for generating transgenic monocots is particle bombardment (microscopic gold or tungsten particles coated with the transforming DNA) of embryonic calli or developing embryos (Christou, 1992, *Plant Journal* 2: 275–281; Shimamoto, 1994, *Current Opinion Biotechnology* 5: 158–162; Vasil et al., 1992, *Bio/Technology* 10: 667–674). An alternative method for transformation of monocots is based on protoplast transformation as described by Omirulleh et al., 1993, *Plant Molecular Biology* 21: 415–428.

Following transformation, the transformants having incorporated therein the expression construct are selected and regenerated into whole plants according to methods well-known in the art.

The present invention also relates to methods for producing a polypeptide of the present invention comprising (a) cultivating a transgenic plant or a plant cell comprising a nucleic acid sequence encoding a polypeptide having cellobiose dehydrogenase activity of the present invention under conditions conducive for production of the polypeptide; and (b) recovering the polypeptide.

Removal or Reduction of Cellobiose Dehydrogenase Activity

The present invention also relates to methods for producing a mutant cell of a parent cell, which comprises disrupting or deleting a nucleic acid sequence of the present invention or a control sequence thereof, which results in the mutant cell producing less of the polypeptide having cellobiose dehydrogenase activity encoded by the nucleic acid sequence than the parent cell when cultivated under the same conditions.

The construction of strains that have reduced cellobiose dehydrogenase activity may be conveniently accomplished by modification or inactivation of a nucleic acid sequence necessary for expression of the polypeptide having cellobiose dehydrogenase activity in the cell. The nucleic acid sequence to be modified or inactivated may be, for example, a nucleic acid sequence encoding the polypeptide or a part thereof essential for exhibiting cellobiose dehydrogenase activity, or the nucleic acid sequence may have a regulatory function required for the expression of the polypeptide from the coding sequence of the nucleic acid sequence. An example of such a regulatory or control sequence may be a promoter sequence or a functional part thereof, i.e., a part which is sufficient for affecting expression of the polypeptide. Other control sequences for possible modification are described above.

Modification or inactivation of the nucleic acid sequence may be performed by subjecting the cell to mutagenesis and selecting or screening for cells in which the cellobiose dehydrogenase producing capability has been reduced. The mutagenesis, which may be specific or random, may be performed, for example, by use of a suitable physical or chemical mutagenizing agent, by use of a suitable oligonucleotide, or by subjecting the DNA sequence to PCR generated mutagenesis. Furthermore, the mutagenesis may be performed by use of any combination of these mutagenizing agents.

Examples of a physical or chemical mutagenizing agent suitable for the present purpose include ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues.

When such agents are used, the mutagenesis is typically performed by incubating the cell to be mutagenized in the presence of the mutagenizing agent of choice under suitable conditions, and selecting for cells exhibiting reduced cellobiose dehydrogenase activity or production.

Modification or inactivation of production of a polypeptide encoded by a nucleic acid sequence of the present invention may be accomplished by introduction, substitution, or removal of one or more nucleotides in the nucleic acid sequence encoding the polypeptide or a regulatory element required for the transcription or translation thereof. For example, nucleotides may be inserted or removed so as to result in the introduction of a stop codon, the removal of the start codon, or a change of the open reading frame. Such modification or inactivation may be accomplished by site-directed mutagenesis or PCR generated mutagenesis in accordance with methods known in the art. Although, in principle, the modification may be performed in vivo, i.e., directly on the cell expressing the nucleic acid sequence to be modified, it is preferred that the modification be performed in vitro as exemplified below.

An example of a convenient way to eliminate or reduce production by a host cell is by gene replacement or gene interruption. In the gene interruption method, a nucleic acid sequence corresponding to the endogenous gene or gene fragment of interest is mutagenized in vitro to produce a defective nucleic acid sequence which is then transformed into the host cell to produce a defective gene. By homologous recombination, the defective nucleic acid sequence replaces the endogenous gene or gene fragment. It may be desirable that the defective gene or gene fragment also encodes a marker which may be used for selection of transformants in which the gene encoding the polypeptide has been modified or destroyed.

Alternatively, modification or inactivation of the nucleic acid sequence may be performed by established anti-sense techniques using a nucleotide sequence complementary to the polypeptide encoding sequence. More specifically, production of the polypeptide by a cell may be reduced or eliminated by introducing a nucleotide sequence complementary to the nucleic acid sequence encoding the polypeptide which may be transcribed in the cell and is capable of hybridizing to the polypeptide mRNA produced in the cell. Under conditions allowing the complementary anti-sense nucleotide sequence to hybridize to the polypeptide mRNA, the amount of polypeptide translated is thus reduced or eliminated.

It is preferred that the cell to be modified in accordance with the methods of the present invention is of microbial origin, for example, a fungal strain which is suitable for the production of desired protein products, either homologous or heterologous to the cell.

The present invention further relates to a mutant cell of a parent cell which comprises a disruption or deletion of a nucleic acid sequence encoding the polypeptide or a control sequence thereof, which results in the mutant cell producing less of the polypeptide than the parent cell.

The polypeptide-deficient mutant cells so created are particularly useful as host cells for the expression of homologous and/or heterologous polypeptides. Therefore, the present invention further relates to methods for producing a homologous or heterologous polypeptide comprising (a) cultivating the mutant cell under conditions conducive for production of the polypeptide; and (b) recovering the polypeptide. The term "heterologous polypeptides" is defined herein as polypeptides which are not native to the host cell, a native protein in which modifications have been made to alter the native sequence, or a native protein whose expression is quantitatively altered as a result of a manipulation of the host cell by recombinant DNA techniques.

In a further aspect, the present invention relates to a method for producing a protein product essentially free of cellobiose dehydrogenase activity by fermentation of a cell which produces both a polypeptide encoded by a nucleic acid sequence of the present invention as well as the protein product of interest by adding an effective amount of an agent capable of inhibiting cellobiose dehydrogenase activity to the fermentation broth before, during, or after the fermentation has been completed, recovering the product of interest from the fermentation broth, and optionally subjecting the recovered product to further purification.

In a further aspect, the present invention relates to a method for producing a protein product essentially free of cellobiose dehydrogenase activity by cultivating the cell under conditions permitting the expression of the product, subjecting the resultant culture broth to a combined pH and temperature treatment so as to reduce the cellobiose dehydrogenase activity substantially, and recovering the product from the culture broth. Alternatively, the combined pH and temperature treatment may be performed on an enzyme preparation recovered from the culture broth. The combined pH and temperature treatment may optionally be used in combination with a treatment with a cellobiose dehydrogenase inhibitor.

In accordance with this aspect of the invention, it is possible to remove at least 60%, preferably at least 75%, more preferably at least 85%, still more preferably at least 95%, and most preferably at least 99% of the cellobiose dehydrogenase activity. Complete removal of cellobiose dehydrogenase activity may be obtained by use of this method.

The combined pH and temperature treatment is preferably carried out at a pH in the range of 6.5–7 and a temperature in the range of 40–70° C. for a sufficient period of time to attain the desired effect, where typically, 30 to 60 minutes is sufficient.

The methods used for cultivation and purification of the product of interest may be performed by methods known in the art.

The methods of the present invention for producing an essentially cellobiose dehydrogenase-free product is of particular interest in the production of eukaryotic polypeptides, in particular fungal proteins such as enzymes. The enzyme may be selected from, e.g., an amylolytic enzyme, lipolytic enzyme, proteolytic enzyme, cellulytic enzyme, oxidoreductase, or plant cell-wall degrading enzyme. Examples of such enzymes include an aminopeptidase, amylase, amyloglucosidase, carbohydrase, carboxypeptidase, catalase, cellulase, chitinase, cutinase, cyclodextrin glycosyltransferase, deoxyribonuclease, esterase, galactosidase, beta-galactosidase, glucoamylase, glucose oxidase, glucosidase, haloperoxidase, hemicellulase, invertase, isomerase, laccase, ligase, lipase, lyase, mannosidase, oxidase, pectinolytic enzyme, peroxidase, phytase, phenoloxidase, polyphenoloxidase, proteolytic enzyme, ribonuclease, transferase, transglutaminase, or xylanase. The cellobiose dehydrogenase-deficient cells may also be used to express heterologous proteins of pharmaceutical interest such as hormones, growth factors, receptors, and the like.

It will be understood that the term "eukaryotic polypeptides" includes not only native polypeptides, but also those polypeptides, e.g., enzymes, which have been modified by amino acid substitutions, deletions or additions, or other such modifications to enhance activity, thermostability, pH tolerance and the like.

In a further aspect, the present invention relates to a protein product essentially free from cellobiose dehydrogenase activity which is produced by a method of the present invention.

Use

The polypeptides encoded by the nucleic acid sequences of the present invention may be used in a pulp bleaching process under alkaline conditions using the methods described in WO 94/01538.

Signal Peptide

The present invention also relates to nucleic acid constructs comprising a gene encoding a protein operably linked to a nucleic acid sequence consisting of nucleotides 71 to 134 of SEQ ID NO:1 encoding a signal peptide consisting of amino acids 1 to 21 of SEQ ID NO:2, wherein the gene is foreign to the nucleic acid sequence.

The present invention also relates to recombinant expression vectors and recombinant host cells comprising such nucleic acid constructs.

The present invention also relates to methods for producing a protein comprising (a) cultivating such a recombinant host cell under conditions suitable for production of the protein; and (b) recovering the protein.

The nucleic acid sequence may be operably linked to foreign genes with other control sequences. Such other control sequences are described above.

The protein may be native or heterologous to a host cell. The term "protein" is not meant herein to refer to a specific length of the encoded product and, therefore, encompasses peptides, oligopeptides, and proteins. The term "protein" also encompasses two or more polypeptides combined to form the encoded product. The proteins also include hybrid polypeptides which comprise a combination of partial or complete polypeptide sequences obtained from at least two different proteins wherein one or more may be heterologous or native to the host cell. Proteins further include naturally occurring allelic and engineered variations of the above mentioned proteins and hybrid proteins.

Preferably, the protein is a hormone, hormone variant, enzyme, receptor or a portion thereof, antibody or a portion thereof, or reporter. In a more preferred embodiment, the protein is an oxidoreductase, transferase, hydrolase, lyase, isomerase, or ligase. In an even more preferred embodiment, the protein is an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, invertase, laccase, lipase, mannosidase, mutanase, oxidase, pectinolytic enzyme, peroxidase, phytase, polyphenoloxidase, proteolytic enzyme, ribonuclease, transglutaminase, or xylanase.

The gene may be obtained from any prokaryotic, eukaryotic, or other source. For purposes of the present invention, the term "obtained from" as used herein in connection with a given source shall mean that the protein is produced by the source or by a cell in which a gene from the source has been inserted.

The present invention is further described by the following examples which should not be construed as limiting the scope of the invention.

EXAMPLES

Materials

Chemicals used as buffers and substrates were commercial products of at least reagent grade.

Example 1

Purification and Characterization of Cellobiose Dehydrogenase from *Humicola insolens*

A solution of CELLUZYME™ (Novo Nordisk A/S, Bagsvaerd, Denmark) containing 21.4 g of protein was applied on a 300 ml arginine Sepharose column equilibrated with 50 mM Tris-HCl buffer, pH 7.0, and eluted with simultaneous gradients of Tris-HCl, pH 7.0–9.0, and 0–0.2M NaCl. The eluate containing the cellobiose dehydrogenase activity was adjusted to pH 5.0 with HCl and applied on an S-Sepharose column in 20 mM Na-citrate pH 5. This column bound most of the cellulases while the cellobiose dehydrogenase was eluted with the eluent. The pH of the eluate was adjusted to 7.0, and the eluate was applied on an anion exchange column (HPQ-Sepharose) previously equilibrated with 50 mM Tris-HCl pH 7.0. The column was eluted with a 0–1 M NaCl gradient. This separated the minor cellobiose dehydrogenase (94 kDa and pI 4.4) from the major (92 kDa and pI of 4.0). Gel filtration on a Superdex 200 Hiload column eluted the cellobiose dehydrogenase with an apparent molecular weight of 92 kDa thus separating it from the contaminating cellulases of lower molecular weight.

Analytical SDS-PAGE of the different fractions was carried out on 10% gel slabs on a Bio-Rad apparatus according to the procedure recommended by the manufacturer with a Tris-glycine buffer system. Electrofocusing was carried out using a LKB multiphore apparatus and ampholine precast gels (LKB). Cellobiose dehydrogenase activity after electrofocusing was determined using a 1% agarose overlayer containing cellobiose and DCPIP. The cellobiose dehydrogenases appeared as distinct clearing zones.

Biochemical Characterization

The amino acid composition was determined using an Applied Biosystems amino acid apparatus. The amino acid composition is shown in Table 1. The values were calculated from the amino acid composition measured after 24 hours of hydrolysis. Tryptophan was determined according to the method of Edelhoch, 1967, *Biochemistry* 6: 1948–1954.

The sample (250 pmole) was hydrolyzed with 1 M HCl at 100° C. for 4 hours. The acid was removed by vacuum evaporation and the identity of the sugars present was established by HPLC with a PAD detector (Dionex Corp. Sunnyvale, U.S.A.) and a Carbopak PAI microcolumn.

The protein is a glycoprotein with a total sugar content of 2% (w/w). The following sugars were detected: 4 moles of glucosamine, 4 moles mannose and 3 moles of galactose per mole enzyme.

TABLE 1

| Amino acid | Cellobiose dehydrogenase from *H. insolens* mol/mol | Cellobiose dehydrogenase from *M. thermophila*[a] mol/mol |
| --- | --- | --- |
| Aspartate | 84 | 114 |
| Threonine | 75 | 66 |
| Serine | 57 | 54 |
| Glutamate | 79 | 54 |
| Proline | 41 | 54 |
| Glycine | 87 | 108 |
| Alanine | 62 | 75 |
| Cysteine | 2 | 9 |
| Valine | 35 | 60 |
| Methionine | 11 | 3 |
| Isoleucine | 23 | 36 |
| Leucine | 54 | 63 |
| Tyrosine | 23 | 30 |
| Phenylalanine | 25 | 36 |
| Lysine | 24 | 36 |
| Histidine | 8 | 12 |
| Arginine | 30 | 30 |
| Tryptophan | 49[b] | Not determined |

[a]Canevascini et al., 1991, European Journal of Biochemistry. 198: 43–52.
[b]Determined according to the method of Edelhoch, 1967, Biochemistry 6: 1948–1954.

Identification of Prosthetic Groups

All absorption spectra and kinetic measurements were recorded on a Hewlett-Packard 8452A Diode Array Spectrophotometer in 0.75 ml black cuvettes with 1 cm optical path. The fluorescence spectra were recorded on a PERKIN ELMER LS 50.

The spectrum of 500 μl of 4.8 μM cellobiose dehydrogenase was recorded and 10 μl of 5 mM cellobiose or a few grains of sodium dithionite were added to give the reduced cellobiose dehydrogenase. For the detection of the flavin group, fluorescence spectra of 1.7 μM cellobiose dehydrogenase were recorded. Emission spectra for the exitation at 397 and 443 nm and exitation spectra for emission at 480 were recorded.

The extinction coefficient of the cellobiose dehydrogenase was estimated to be $\epsilon_{280}$=330,000 $M^{-1}.cm^{-1}$ using the amino acid composition and a molecular weight of 85 kDa.

Two extinction coefficients were measured for DCPIP: in the range pH 2 to 5.5 $\epsilon_{530}$=7,500 $M^{-1}.cm^{-1}$ and from pH 5.5 to 10 $\epsilon_{600}$=14,000 $M^{-1}.cm^{-1}$. Potassium ferricyanide (Merck): $\epsilon_{420}$=970 $M^{-1}.cm^{-1}$, 3,5-di-tert-butyl-1,2-benzoquinone (Merck): $\epsilon_{410}$=1,400 $M^{-1}.cm^{-1}$, Methylene Blue (Merck): $\epsilon_{610}$=42,000 $M^{-1}.cm^{-1}$, cytochrome c (Sigma, from horse heart): $\epsilon_{550}$=8,000 $M^{-1}.cm^{-1}$.

The visible spectrum of the cellobiose dehydrogenase was characteristic of a hemoprotein. The oxidized state had an absorption maximum at 420 nm (γ band 203,000 $M^{-1}.cm^{-1}$) while the spectra of the reduced state showed absorption peaks at 564 nm (α band, 61,000 $M^{-1}.cm^{-1}$), 534 nm (β band, 46,000 $M^{-1}.cm^{-1}$) and 432 nm (γ band, 287,000 $M^{-1}.cm^{-1}$) which was typical of a cytochrome b (cf. G. Canevascini et al., 1991, *European Journal of Biochemistry* 198: 43). The flavin group was weakly fluorescent, with an emission maximum at 480 nm and exitation maxima at 397 and 443 nm.

Determination of Cellobiose Dehydrogenase Activity

The measurements were performed in 0.1 M sodium phosphate pH 7.5 buffer at 40° C. Specifically, 450 μl of a mixture of 100 μM of 2,6-dichlorophenolindophenol (DCPIP, Merck) and 250 μM of cellobiose (Sigma) was mixed with 50 μl of nzyme. One unit of cellobiose dehydrogenase activity equals 1.0 μmole of cellobiose oxidized (DCPIP reduced) per minute at pH 7.5, 40° C.

Identification of Oxidation Product and Catalytic Properties

A total of 40 mg of cellobiose was mixed with 30 mg of DCPIP in 10 ml water and 100 μl of 1.6 μM cellobiose dehydrogenase was added. The mixture was stirred overnight at room temperature. The mixture was diluted with water and extracted several times with ethyl acetate to remove the reduced and non-reduced DCPIP. $^1H$ NMR and $^{13}C$ NMR spectra of cellobiose and the oxidized product in $D_2O$ were then taken on a Bruker ACP 300 spectrometer. Cellobiose: $^1H$ NMR ($D_2O$): δ (ppm) 4.65 (β, H-1, $J_{1,2}$=8.0 Hz), 5.21 (α,H-1,$J_{1,2}$=3.7 HZ) (Claeyssens et al., 1990); $_{13}C$ NMR ($D_2O$): δ (ppm) 92.9 (α,C-1) 96.8 (β,C-1) (Dorman and Roberts, 1971). Cellobionolactone: $^1H$ NMR ($D_2O$): no peaks between 4.28 ppm and 4.75 ppm (H-1', $J_{1',2'}$=8.0 HZ); $^{13}C$ NMR ($D_2O$): δ (ppm) no peaks between 84.2 ppm (C-4) and 105.5 ppm (C-1').

All measurements were performed in 0.1 M sodium phosphate pH 7.5 buffer at 40° C. 450 μl of 15 μM to 5 mM (depending on $K_m$) of electron donors and acceptors and 50 μg of 70 nM to 200 nM of enzyme depending on $k_{cat}$ were mixed to a total volume of 500 μl. The reactions were monitored for 400 s as changes in absorbance at the appropriate wavelength (see above). The benzoquinone was dissolved in ethanol to a concentration of 10 mM and diluted in phosphate buffer to the appropriate concentration. The catalytic constants ($k_{cat}$) were expressed as mol of oxidized cellobiose/s/mol of enzyme. One equivalent of DCPIP, Methylene Blue, or benzoquinone oxidizes one equivalent of cellobiose whereas two equivalents of cytochrome c or ferricyanide oxidizes one equivalent of cellobiose. The kinetic constants were determined using Lineweaver-Burke plots and were the result of dual determinations.

The enzyme was found to be able to oxidize different disaccharides and cellodextrins as listed in Table 2, but was unable to oxidize glucose. The product of the oxidation of cellobiose was identified using $^1H$ and $^{13}C$ NMR in $D_2O$. In both spectra the peaks corresponding to the α- and β-anomer of the reducing end had disappeared implying oxidation at C-1 resulting in cellobionic acid.

Cellobiose and the cellodextrins were readily oxidized by the cellobiose dehydrogenase with approximately the same $k_{cat}$ and $K_m$ independent of the degree of polymerization as seen in Table 2. Lactose was oxidized at a rate comparable to those of the cellodextrins. Maltose and xylobiose were also substrates. However, these substrates displayed a significantly weaker binding than that of the cellodextrins. Glucose, N,N-diacetylchitobiose, and N-acetyllactosamine were not oxidized.

TABLE 2

| Electron donor Sugar + 90 μM DCPIP | $K_m$ (μM) | $k_{cat}$ ($s^{-1}$) |
|---|---|---|
| Cellobiose | 11 | 10 |
| Cellotriose | 19 | 8.5 |
| Cellotetraose | 21 | 8.5 |
| Cellopentaose | 17 | 8.3 |
| Lactose | 51 | 10 |
| Maltose | 11,000 | 0.83 |
| Xylobiose | 7,100 | 2.15 |
| N,N-Diacetylchitobiose | — | 0 |
| N-Acetyllactosamine | — | 0 |
| Glucose | — | 0 |

TABLE 3

| Electron acceptor + 225 μM cellobiose | $K_m$ (μM) | $k_{cat}$ ($s^{-1}$) |
|---|---|---|
| DCPIP | 26 | 12 |
| Methylene Blue | 18 | 1.85 |
| Benzoquinone | 132 | 15 |
| Ferricyanide | 12 | 10 |
| Cytochrome c | 93 | 19 |

Determination of Temperature and pH Activity Profiles

For temperature activity the measurement was performed in 0.1 M glycine pH 9.5 buffer at different temperatures using 550 μM cytochrome C (horse heart, Sigma Chemical Co., St. Louis, Mo.), 225 μM cellobiose (Sigma Chemical Co., St. Louis, Mo.) and enzyme in a total volume of 500 μl. The activity was measured as reduction of cytochrome c using a molar extinction coefficient of 8,000 $M^{-1}.cm^{-1}$. Optimal activity was found at 55° C. during 5 minutes incubation as shown in FIG. 1.

Figure 2:
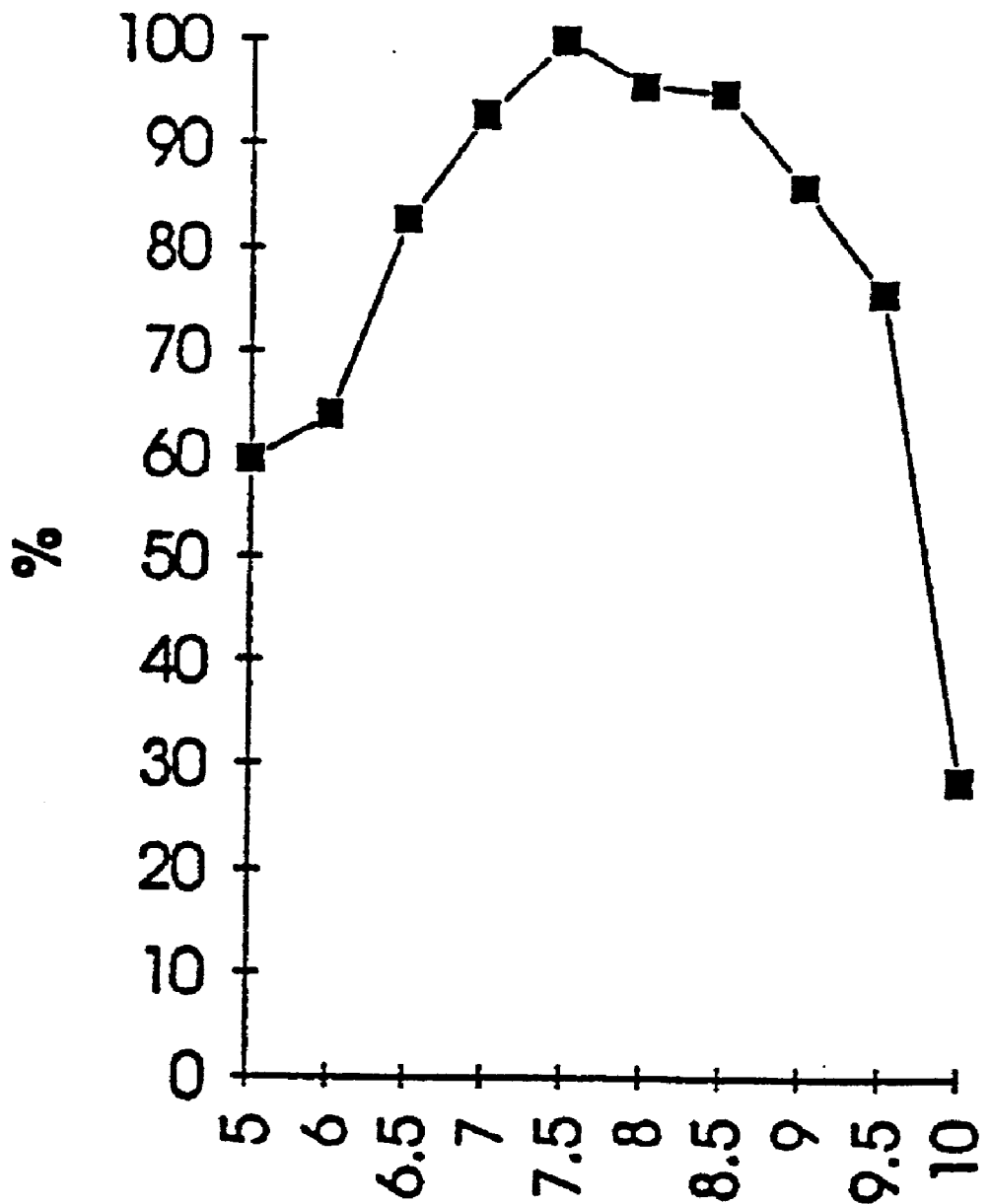
FIG. 2 shows the pH activity profile of a *Humicola insolens* DSM 1800 cellobiose dehydrogenase at 40° C.

The pH activity profile was measured at 40° C. activity using sodium acetate buffer from pH 3.5 to 6.5, sodium phosphate from pH 6.5 to 8.5 and glycine buffer from pH 9 to 10. All buffers at 0.1 M concentration and the enzyme and cellobiose and cytochrome c concentration as above. Optimum activity was obtained at pH 7.5 and 75% residual activity was obtained at pH 9.5 as shown in FIG. 2. The steady state kinetics were followed for 10 minutes.

Example 2

Amino Acid Sequencing of *Humicola insolens* Cellobiose Dehydrogenase

N-terminal sequencing of a semi-purified preparation of the cellobiose dehydrogenase and digested fragments of the cellobiose dehydrogenase was performed on an Applied Biosystems 476A Protein Sequencer (Perkin Elmer/Applied Biosystems Division, Foster City, Calif.) with on-line HPLC and liquid phase trifluoroacetic acid (TFA) delivery. Samples of the cellobiose dehydrogenase were transblotted onto Novex PVDF membranes (Novex, San Diego, Calif.) from SDS-PAGE gels using 10 mM CAPS (3-[cyclohexylamino]-1-propanesulfonic acid) in 10% methanol, pH 11.0 for 2 hours at 25 volts. The PVDF membrane was stained with 0.1% Commassie Blue R-250 in 40% methanol/1% acetic acid for 20 seconds and destained in 50% ethanol to observe the protein bands. Stained protein bands were excised and sequenced from a blott cartridge using sequencing reagents (Perkin Elmer/Applied Biosystems Division, Foster City, Calif.). Detection of phenylthiohydantoinamino acids was accomplished by on-line HPLC using Buffer A containing 3.5% tetrahydrofuran in water with 18 ml of the Premix concentrate (Perkin Elmer/Applied Biosystems Division, Foster City, Calif.) containing acetic acid, sodium acetate, and sodium hexanesulfonate and Buffer B containing acetonitrile. Data was collected and analyzed on a Macintosh IIsi using Applied Biosystems 610 Data Analysis Software. Amino acid identifications were performed by visualizing chromatograms against a light source and determined by the operator.

The 90 kd protein band of the purified cellobiose dehydrogenase was apparently N-terminally blocked. The purified cellobiose dehydrogenase was then subjected to cyanogen bromide and Endoproteinase Glu-C digestions to generate peptide fragments of the enzyme for sequencing. The cellobiose dehydrogenase was digested with cyanogen bromide by reconstituting a dried sample of the purified cellobiose dehydrogenase in 70% formic acid with a few crystals of cyanogen bromide added and incubating for 18 hours at room temperature in the dark. The peptide fragments were separated by SDS-PAGE electrophoresis using 10–20% Novex Tricine gels (Novex, San Diego, Calif.) under reducing conditions and blot transferred to PVDF membrane as described above. Peptide fragments corresponding to 40, 20, 17, 15, and 6 kd were excised and subjected to n-terminal sequencing. All peptide fragments except a 20 kd fragment were found to be N-terminally blocked or not determined. The N-terminal sequence of the 20 kd fragment was determined to be FAGGERNG-PLATYLVSADARENFSL (Peptide 1) (SEQ ID NO. 2).

The purified cellobiose dehydrogenase was partially digested with sequencing grade Endoproteinase Glu-C from *Staphylococcus aureus;* (Boehringer Mannheim GmbH, Germany) in 0.125 M Tris-HCl, 0.25% SDS, pH 6.7 for 2 hours at room temperature. The peptide fragments were separated by reverse-phase HPLC using a Hewlett Packard 1090L HPLC (Hewlett Packard GmbH, Germany) with a 5 micron, 2.1×250 mm Vydac C18 reverse-phase column (Vydac, Hesperia, Calif.). A step gradient was used with 0.06% TFA and 0.05% TFA in 80% acetonitrile as the eluants. The peptide samples were hand-collected and then subjected to N-terminal sequencing as described.

Three peptides were recovered.

Peptide 2: RIPG(T or Y)(W or L)(H or G)(P or R)(S or G)MDGKLYRDE (SEQ ID NO. 2).
Peptide 3: WASLPGLTVE (SEQ ID NO. 2), and
Peptide 4: GWH(S or R)QDLAAATERVF (SEQ ID NO. 2)

Example 3

Construction of the *Humicola insolens* cDNA Library in the Yeast Expression Vector pYES 2.0

*Humicola insolens* strain DSM 1800 was grown as described in WO97/32014. The mycelium was harvested after 5 days growth at 26° C., immediately frozen in liquid $N_2$, and stored at −80° C.

All glassware used in the RNA isolations were baked at 220° C. for at least 12 hours. Eppendorf tubes, pipet tips and plastic columns were treated in 0.1% diethylpyrocarbonate in ethanol for 12 hours, and autoclaved. All buffers and water (except Tris-containing buffers) were treated with 0.1% diethylpyrocarbonate for 12 hours at 37° C., and autoclaved.

The total RNA was prepared by extraction with guanidinium thiocyanate followed by ultracentrifugation through a 5.7 M cesium chloride cushion (Chirgwin et al., 1979, *Biochemistry* 18: 5294–5299) using the following modifications. The frozen mycelia were ground in liquid $N_2$ to a fine powder with a mortar and a pestle, followed by grinding in a precooled coffee mill, and immediately suspended in 5 volumes of RNA extraction buffer (4 M guanidinium thiocyanate, 0.5% sodium laurylsarcosine, 25 mM sodium citrate pH 7.0, 0.1 M β-mercaptoethanol). The mixture was stirred for 30 minutes at room temperature and centrifuged (30 minutes, 5000 rpm, room temperature, Heraeus Megafuge 1.0 R) to pellet the cell debris. The supernatant was collected, carefully layered onto a 5.7 M cesium chloride cushion (5.7 M cesium chloride, 0.1 M EDTA, pH 7.5, 0.1% diethylpyrocarbonate; autoclaved prior to use) using 26.5 ml supernatant per 12.0 ml cesium chloride cushion, and centrifuged to obtain the total RNA (Beckman, SW 28 rotor, 25 000 rpm, room temperature, 24 hours). After centrifugation the supernatant was carefully removed and the bottom of the tube containing the RNA pellet was cut off and rinsed with 70% ethanol. The total RNA pellet was transferred into an Eppendorf tube, suspended in 500 μl of 10 mM Tris-1 mM EDTA pH 7.6 (TE) (if difficult, heat occasionally for 5 minutes at 65° C.), phenol extracted and precipitated with ethanol for 12 hours at −20° C. (2.5 volumes ethanol, 0.1 volume 3 M sodium acetate pH 5.2). The RNA was collected by centrifugation, washed in 70% ethanol, and resuspended in a minimum volume of 0.1% diethylpyrocarbonate. The RNA concentration was determined by measuring OD 260/280.

The poly(A)+ RNAs were isolated by oligo(dT)-cellulose affinity chromatography (Aviv & Leder, 1972, *Proceedings of the National Academy Sciences USA* 69: 1408–1412). Typically, 0.2 g of oligo(dT) cellulose (Boehringer Mannheim, Indianapolis, Ind.) was preswollen in 10 ml of 1× column loading buffer (20 mM Tris-Cl pH 7.6, 0.5 M NaCl, 1 mM EDTA, 0.1% SDS), loaded onto a 0.1% diethylpyrocarbonate-treated, plugged plastic column (Poly Prep Chromatography Column, BioRad, Hercules, Calif.), and equilibrated with 20 ml of 1× loading buffer. The total RNA was heated at 65° C. for 8 minutes, quenched on ice for 5 minutes, and after addition of 1 volume of 2×column loading buffer to the RNA sample loaded onto the column. The eluate was collected and reloaded 2–3 times by heating the sample as above and quenching on ice prior to each loading. The oligo(dT) column was washed with 10 volumes of 1× loading buffer, then with 3 volumes of medium salt buffer (20 mM Tris-Cl pH 7.6, 0.1 M sodium chloride, 1 mM EDTA, 0.1% SDS), followed by elution of the poly(A)+ RNA with 3 volumes of elution buffer (10 mM Tris-Cl pH 7.6, 1 mM EDTA, 0.05% SDS) preheated to 65° C., by collecting 500 μl fractions. The $OD_{260}$ was read for each collected fraction, and the mRNA containing fractions were pooled and ethanol precipitated at −20° C. for 12 hours. The poly(A)+ RNA was collected by centrifugation, resuspended in 0.1% diethylpyrocarbonate, and stored in 5–10 μg aliquots at −80° C.

cDNA first strand synthesis: Double-stranded cDNA was synthesized from 5 µg of *Aspergillus aculeatus* (SP249)/ *Trichoderma harzianum* (SP234) poly(A)+ RNA by the RNase H method using the hair-pin modification (Gubler and Hoffman 1983, *Gene* 25: 263–269; Sambrook et al., 1989, supra). The poly(A)+ RNA (5 µg in 5 µl of 0.1% diethylpyrocarbonate-treated water) was heated at 70° C. for 8 minutes, quenched on ice, and combined in a final volume of 50 µl with reverse transcriptase buffer (50 mM Tris-Cl pH 8.3, 75 mM potassium chloride, 3 mM magnesium chloride, 10 mM DTT, (Life Technologies, Gaithersburg, Md.) containing 1 mM each dNTP (Pharmacia, Piscataway, N.J.), 40 units of human placental ribonuclease inhibitor (RNasin, Promega, Madison, Wis.), 10 µg of oligo(dT)12–18 primer (Pharmacia, Piscataway, N.J.) and 1000 units of SuperScript II RNase H-reverse transcriptase (Life Technologies, Gaithersburg, Md.). First-strand cDNA was synthesized by incubating the reaction mixture at 45° C. for 1 hour.

cDNA second strand synthesis: After first-strand cDNA synthesis, 30 µl of 10 mM Tris-Cl pH 7.5, 1 mM EDTA was added, and the mRNA:cDNA hybrids were ethanol precipitated for 12 hours at −20° C. by addition of 40 mg glycogen carrier (Boehringer Mannheim, Indianapolis, Ind.) 0.2 volumes of 10 M ammonium acetate and 2.5 volumes of 96% ethanol. The hybrids were recovered by centrifugation, washed in 70% ethanol, air dried, and resuspended in 250 µl of second strand buffer (20 mM Tris-Cl pH 7.4, 90 mM potassium chloride, 4.6 mM magnesium chloride, 10 mM ammonium sulfate, 16 µM βNAD+) containing 100 µM each dNTP, 44 units of *E. coli* DNA polymerase I (Amersham, Arlington Heights, Ill.), 6.25 units of RNase H (Life Technologies, Gaithersburg, Md.), and 10.5 units of *E. coli* DNA ligase (New England Biolabs, Beverly, Mass.). Second strand cDNA synthesis was performed by incubating the reaction tube at 16° C. for 3 hours, and the reaction was stopped by addition of EDTA to 20 mM final concentration followed by phenol extraction.

The double-stranded cDNA was ethanol precipitated at −20° C. for 12 hours by addition of 2 volumes of 96% ethanol, 0.1 volume of 3 M sodium acetate pH 5.2, recovered by centrifugation, washed in 70% ethanol, dried (SpeedVac), and resuspended in 30 µl of Mung bean nuclease buffer (30 mM sodium acetate pH 4.6, 300 mM sodium chloride, 1 mM zinc sulfate, 0.35 mM DTT, 2% glycerol) containing 36 units of Mung bean nuclease (Life Technologies, Gaithersburg, Md.). The single-stranded hair-pin DNA was clipped by incubating the reaction at 30° C. for 30 minutes, followed by addition of 70 µl 10 mM Tris-Cl pH 7.5, 1 mM EDTA, phenol extraction, and ethanol precipitation with 2 volumes of 96% ethanol and 0.1 volume of 3 M sodium acetate pH 5.2 at −20° C. for 12 hours.

The double-stranded cDNA was blunt-ended with T4 DNA polymerase in 50 µl of T4 DNA polymerase buffer (20 mM Tris-acetate pH 7.9, 10 mM magnesium acetate, 50 mM potassium acetate, 1 mM DTT) containing 0.5 mM each dNTP, and 7.5 units of T4 DNA polymerase (Invitrogen, Carlsbad, Calif.) by incubating the reaction mixture at 37° C. for 15 minutes. The reaction was stopped by addition of EDTA to 20 mM final concentration, followed by phenol extraction and ethanol precipitation.

After the fill-in reaction the cDNA was ligated to non-palindromic BstX I adaptors (1 µg/µl, Invitrogen, Carlsbad, Calif.) in 30 µl of ligation buffer (50 mM Tris-Cl pH 7.8, 10 mM magnesium chloride, 10 mM DTT, 1 mM ATP, 25 µg/ml bovine serum albumin) containing 600 pmol BstX I adaptors and 5 units of T4 ligase (Invitrogen, Carlsbad, Calif.) by incubating the reaction mix at 16° C. for 12 hours. The reaction was stopped by heating at 70° C. for 5 minutes, and the adapted cDNA was size-fractionated by agarose gel electrophoresis (0.8% HSB-agarose, FMC, Rockville, Md.) to separate unligated adaptors and small cDNAs. The cDNA was size-selected with a cut-off at 0.7 kb, and the cDNA was electroeluted from the agarose gel in 10 mM Tris-Cl pH 7.5, 1 mM EDTA for 1 hour at 100 volts, phenol extracted, and ethanol precipitated at −20° C. for 12 hours as above.

The adapted, double-stranded cDNA was recovered by centrifugation, washed in 70% ethanol, and resuspended in 25 µl deionized water. Prior to large-scale library ligation, four test ligations were carried out in 10 µl of ligation buffer (same as above) each containing 1 µl of double-stranded cDNA (reaction tubes #1–#3), 2 units of T4 ligase (Invitrogen) and 50 ng (tube #1), 100 ng (tube #2) and 200 ng (tubes #3 and #4) BstXI cleaved pYES 2.0 vector (Invitrogen, Carlsbad, Calif.). The ligation reactions were performed by incubation at 16° C. for 12 hours, heated at 70° C. for 5 minutes, and 1 µl of each ligation electroporated (200Ω, 2.5 kV, 25 µF) to 40 µl competent *E. coli* 1061 cells ($OD_{600}$=0.9 in 1 liter LB broth, washed twice in cold deionized water, once in 20 ml of 10% glycerol, resuspended in 2 ml of 10% glycerol). After addition of 1 ml of SOC medium to each transformation mix, the cells were grown at 37° C. for 1 hour, 50 µl plated on LB plus ampicillin plates (100 µg/ml), and grown at 37° C. for 12 hours. SOC medium was composed per liter of 20 g of bactotryptone, 5 g of bacto yeast extract, 0.58 g of NaCl, 0.19 g of KCl, which was adjusted to pH 7.0 and autoclaved; then glucose to 20 mM, $MgCl_2$ to 10 mM, and $MgSO_4$ to 10 mM were added.

Using the optimal conditions a large-scale ligation was set up in 40 µl of ligation buffer containing 9 units of T4 ligase, and the reaction was incubated at 16° C. for 12 hours. The ligation reaction was stopped by heating at 70° C. for 5 minutes, ethanol precipitated at −20° C. for 12 hours, recovered by centrifugation and resuspended in 10 µl of deionized water. One µl aliquots were transformed into electrocompetent *E. coli* 1061 cells using the same electroporation conditions as above, and the transformed cells were titered and the library plated on LB plus ampicillin plates with 5000–7000 c.f.u./plate. The cDNA library was stored as (1) individual pools (5000–7000 c.f.u./pool) in 20% glycerol at −80° C., (2) cell pellets of the same pools at −20° C., and (3) Qiaex II purified plasmid DNA (Qiagen, Santa Clarita, Calif.) from individual pools at −20° C. (Qiagen Tip 100, Diagen).

Example 4

Genomic DNA Extraction

Agar slants of *Humicola insolens* DSM 1800 mycelia were rinsed with 10 ml of 0.008% Tween 20. A 2 ml volume of the mycelial suspension was inoculated into a 250 ml glass shake flask containing 50 ml of MY50 pH 6.0 medium and incubated at 26° C., 125 rpm for 6 days. MY50 medium was composed per liter of 50 g of maltodextrin, 2 g of $MgSO_4.7H_2O$, 10 g of $KH_2PO_4$, 2 g of $K_2SO_4$, 2 g of citric acid, 10 g of yeast extract, 2 g of urea, and 0.5 ml of AMG trace elements. The AMG trace elements solution was composed per liter of 14.3 g of $ZnSO_4.7H_2O$, 2.5 g of $CuSO_4.5H_2O$, 0.5 g of $NiCl_2.6H_2O$, 13.8 g of $FeSO_4.7H_2O$, 8.5 g of $MnSO_4.H_2O$, and 3 g of citric acid.

DNA was extracted according to the method of Wahle-ithner et al., 1996, *Current Genetics* 29: 395–403.

Example 5

PCR Amplification of *Humicola insolens* Cellobiose Dehydrogenase

Based on the amino acid sequences of the *Humicola insolens* partial peptides described in Example 2, the degenerate oligonucleotide primers shown below were synthesized by Operon (Alameda, Calif.) to PCR amplify cellobiose dehydrogenase gene fragments from the *Humicola insolens* genomic DNA described in Example 4.

Forward primer: 5'-ATGGAYGGNAARYTNTAYMGNGAYGA-3' (SEQ ID NO:3)

Reverse primer: 5'-AARTTYTCNCKNGCRTCNGC-3' (SEQ ID NO:4)

(R=A or G, Y=C or T, M=A or C, K=G or T, N=Inosine)

Amplification was accomplished using the Hot Wax Optistart Kit (Invitrogen, San Diego, Calif.) according to the manufacturer's instructions. Six reactions were set up that differ from each other by pH and $Mg^{2+}$ concentration as shown below:

|        | 1.5 mM $Mg^{2+}$ | 2.5 mM $Mg^{2+}$ | 3.5 mM $Mg^{2+}$ |
|--------|------------------|------------------|------------------|
| pH 8.5 | reaction 1       | reaction 2       | reaction 3       |
| pH 9   |                  | reaction 4       |                  |
| pH 9.5 |                  | reaction 5       |                  |
| pH 10  |                  | reaction 6       |                  |

The 50 μl amplification reactions contained 1.4 μg of the *Humicola insolens* genomic DNA as the template, 50 pM of each primer, 1× PCR Buffer, 5 μl of 10 mM dNTP, and a wax bead containing the appropriate amount of $Mg^{2+}$. The reactions were cycled in a Perkin Elmer 480 Thermal Cycler programmed for 1 cycle at 94° C. for 2.5 minutes, 37° C. for 3 seconds, and 72° C. for 45 seconds; 25 cycles each at 94° C. for 30 seconds, 37° C. for 30 seconds, and 72° C. for 45 minutes; and 1 cycle at 94° C. for 30 seconds, 37° C. for 30 seconds, and 72° C. for 6 minutes. The last cycle was a 4° C. soak.

A 9 μl volume from each reaction was electrophoresed for 1 hour at 100 volts on a 1% agarose gel. Reactions 1 through 6 revealed a major band at about 200 bp. The six reactions were pooled and electrophoresed for 1 hour at 100 volts on a 2% agarose gel. The band was excised from the gel and purified using Qiaex II. The purified PCR product was subsequently cloned into plasmid pCR2.1-TOPO (Invitrogen, San Diego, Calif.) and transformed into TOP10 cells (Invitrogen, Carlsbad, Calif.) according to the manufacturer's instructions.

The *Humicola insolens* gene segment (204 bp) consisting of 68 codons was amplified from *Humicola insolens* genomic DNA with the cellobiose dehydrogenase-specific PCR primers described above. DNA sequence analysis showed that the amplified gene segment encoded a portion of the corresponding *Humicola insolens* cellobiose dehydrogenase gene. The cellobiose dehydrogenase gene segment was used to probe a *Humicola insolens* cDNA library described in Example 4.

Example 6

Identification of Cellobiose Dehydrogenase Clones

The *Humicola insolens* cDNA library described in Example 3 was used to transform *E. coli* XL1-blue cells (Stratagene, La Jolla, Calif.) which were plated on LB medium supplemented with 100 μg/ml ampicillin agar plates. Colony lifts (Maniatis et al., 1982, *Molecular Cloning, A Laboratory Manual,* Cold Spring Harbor Press, Cold Spring Harbor, N.Y.) were performed on approximately 50,000 colonies and the DNA was cross-linked onto membranes (Hybond N+, Amersham, Arlington Heights, Ill.) using a UV Stratalinker (Stratagene, La Jolla, Calif.). The membranes were soaked 2 hours at 55° C. in a hybridization solution containing 5× SSPEE, 0.3% SDS, 50% formamide, and 10 μg/ml of denatured and sheared herring testes DNA. The cellobiose dehydrogenase gene fragment isolated from *Humicola insolens* as described in Example 5 was radiolabeled using the Prime IT II Labeling Kit (Stratagene, La Jolla, Calif.), denatured by adding NaOH to a final concentration of 0.1 M, and added to the hybridization solution at an activity of approximately $1\times10^6$ cpm per ml of hybridization solution. The mixture was incubated overnight at 55° C. in a shaking water bath. Following incubation, the membranes were washed three times in 2× SSC, 0.2% SDS at 55° C. The membranes were then dried on blotting paper for 15 minutes, wrapped in SaranWrap™, and exposed to X-ray film for 5 hours at −70° C. with intensifying screens (Kodak, Rochester, N.Y.).

Sixteen colonies produced strong hybridization signals with the probe. A plug around the colonies was removed and inoculated into one ml of LB medium supplemented with 100 μg of ampicillin per ml of medium. Dilutions of $10^{-4}$, $10^{-5}$, and $10^{-6}$ were made with each plug solution. One hundred μl of each dilution was plated on LB agar plates supplemented with 100 μg of ampicillin per ml of medium. The dilution for each positive which produced about 100 colonies per plate were chosen for secondary lifts. The lifts were prepared, hybridized, and probed as above, except the hybridization and wash temperature was 62° C. and the hybridization took place over the weekend. The membranes were then dried on blotting paper for 15 minutes, wrapped in SaranWrap™, and exposed to X-ray film overnight at −70° C. with intensifying screens.

Eight of the lifts produced strong hybridization signals with the probe. Two colonies from each positive plate were inoculated into three ml of LB medium supplemented with 100 μg of ampicillin per ml of medium and grown for 16 hours at 37° C. Miniprep DNA was prepared on the Qiagen Bio Robot 9600. Seven clones contained cellobiose dehydrogenase encoding sequence, as confirmed by DNA sequencing, and one clone (pEJG44) was full length. The *E. coli* colony containing the pEJG44 plasmid was isolated and plasmid DNA was prepared using a Qiagen Maxi Prep according to the manufacturer's instructions for sequencing.

Example 7

DNA Sequence Analysis of the *Humicola insolens* Cellobiose Dehydrogenase cDNA Clone DNA sequencing was performed with an Applied Biosystems Model 377 XL Automated DNA Sequencer using dye-terminator chemistry. Contiguous sequences were generated using a transposon insertion strategy (Primer Island Transposition Kit, Perkin-Elmer/Applied Biosystems, Inc., Foster City, Calif.). The cellobiose dehydrogenase clone from pEJG44 was sequenced to an average redundancy of 5.

The nucleotide sequence of the gene encoding the *Humicola insolens* cellobiose dehydrogenase and the deduced amino acid sequence thereof is shown in FIGS. 3A, B, and C (SEQ ID NOS:1 and 2, respectively). Sequence analysis of the cloned insert revealed a large open reading frame of 2355 nucleotides (excluding the stop codon) encoding a protein of 785 amino acids sequence (SEQ ID NO:2). The G+C content of this open reading frame was 61%. Based on the rules of van Heijne (van Heijne, 1984, *Journal of Molecular Biology* 173: 243–251), there appears to be a secretory signal peptide of 21 amino acids which directs the nascent polypeptide into the endoplasmic reticulum.

The amino acid sequences of the partial peptides derived from the cellobiose dehydrogenase described in Example 2 were consistent with those found in the deduced amino acid sequence (SEQ ID NO:2) of the *Humicola insolens* cellobiose dehydrogenase cDNA.

A comparative alignment of cellobiose dehydrogenase sequences was undertaken using the Clustal method (Higgins, 1989, *CABIOS* 5: 151–153) using the LASERGENE™ MEGALIGN™ software (DNASTAR, Inc., Madison, Wis.) with an identity table and the following multiple alignment parameters: Gap penalty of 10, and gap length penalty of 10. Pairwise alignment parameters were Ktuple=1, gap penalty=3, windows=5, and diagonals=5.

The comparative alignment showed that the *Humicola insolens* cellobiose dehydrogenase shared regions of identity with two cellobiose dehydrogenase proteins from Phanerochaete of 30.4% and 31.8% (accession numbers U65888 and U46081, respectively) and with a Trametes cellobiose dehydrogenase of 31.1% (accession number AF029668).

Deposit of Biological Material

The following biological material has been deposited under the terms of the Budapest Treaty with the Agricultural Research Service Patent Culture Collection, Northern Regional Research Center, 1815 University Street, Peoria, Ill., 61604, and given the following accession number:

| Deposit | Accession Number | Date of Deposit |
|---|---|---|
| *E. coli* XLI-blue pEJG44 | NRRL B-30065 | October 27, 1998 |

The strain has been deposited under conditions that assure that access to the culture will be available during the pendency of this patent application to one determined by the Commissioner of Patents and Trademarks to be entitled thereto under 37 C.F.R. §1.14 and 35 U.S.C. §122. The deposit represents a substantially pure culture of the deposited strain. The deposit is available as required by foreign patent laws in countries wherein counterparts of the subject application, or its progeny are filed. However, it should be understood that the availability of a deposit does not constitute a license to practice the subject invention in derogation of patent rights granted by governmental action.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

What is claimed is:

1. An isolated nucleic acid sequence encoding a polypeptide having cellobiose dehydrogenase activity, selected from the group consisting of:

(a) a nucleic acid sequence encoding a polypeptide having an amino acid sequence which has at least 70% identity with amino acids 22 to 785 of SEQ ID NO:2;

(b) a nucleic acid sequence having at least 70% homology with nucleotides 135 to 2425 of SEQ ID NO:1;

(c) a nucleic acid sequence which hybridizes under low stringency conditions with (i) nucleotides 135 to 2425 of SEQ ID NO:1, (ii) the genomic sequence comprising nucleotides 135 to 2425 of SEQ ID NO.1, (iii) a subsequence of (i) or (ii) of at least 100 nucleotides, or (iv) a complementary strand of (i), (ii), or (iii);

(d) a subsequence of (a), (b), or (c), wherein the subsequence encodes a polypeptide fragment which has cellobiose dehydrogenase activity; and (e) a nucleic acid sequence encoding the polypeptide of SEQ ID NO:2 having cellobiose dehydrogenase activity with a pH optimum at a pH of about 5–9 using DCPIP or benzoquinones as the electron acceptor, about pH 7–9 using cytochrome C as the electron acceptor; and about pH 9 using ferric cyanide as the electron acceptor; a temperature optimum of 55° C. at pH 9.5, a molecular weight of about 92 kDa by SDS-PAGE; anisoelectric point of about 4–5; a relative activity of at least 70% at a pH of about 9 and a temperature of about 50° C.; and stability at a pH of 5–10.

2. The nucleic acid sequence of claim 1, which encodes a polypeptide having an amino acid sequence which has at least 70% identity with amino acids 22 to 785 of SEQ ID NO:2.

3. The nucleic acid sequence of claim 2, which encodes a polypeptide having an amino acid sequence which has at least 80% identity with amino acids 22 to 785 of SEQ ID NO:2.

4. The nucleic acid sequence of claim 3, which encodes a polypeptide having an amino acid sequence which has at least 90% identity with amino acids 22 to 785 of SEQ ID NO:2.

5. The nucleic acid sequence of claim 4, which encodes a polypeptide having an amino acid sequence which has at least 95% identity with amino acids 22 to 785 of SEQ ID NO:2.

6. The nucleic acid sequence of claim 1, which encodes a polypeptide comprising the amino acid sequence of SEQ ID NO:2.

7. The nucleic acid sequence of claim 1, which encodes a polypeptide consisting of the amino acid sequence of SEQ ID NO:2, or a fragment thereof which has cellobiose dehydrogenase activity.

8. The nucleic acid sequence of claim 7, which encodes a polypeptide consisting of the amino acid sequence of SEQ ID NO:2.

9. The nucleic acid sequence of claim 8, which encodes a polypeptide consisting of amino acid 22 to 785 of SEQ ID NO:2.

10. The nucleic acid sequence of claim 1, which has at least 70% homology with nucleotides 135 to 2425 of SEQ ID NO:1.

11. The nucleic acid sequence of claim 10, which has at least 80% homology with nucleotides 135 to 2425 of SEQ ID NO:1.

12. The nucleic acid sequence of claim 11, which has at least 90% homology with nucleotides 135 to 2425 of SEQ ID NO:1.

13. The nucleic acid sequence of claim 12, which has at least 95% homology with nucleotides 135 to 2425 of SEQ ID NO:1.

14. The nucleic acid sequence of claim 1, which has the nucleic acid sequence of SEQ ID NO:1.

15. The nucleic acid sequence of claim 1, wherein the nucleic acid sequence hybridizes under medium stringency conditions with (i) nucleotides 135 to 2425 of SEQ ID NO:1, (ii) the genomic sequence comprising nucleotides 135 to 2425 of SEQ ID NO.1, (iii) a subsequence of (i) or (ii) of at least 100 nucleotides, or (iv) a complementary strand of (i), (ii), or (iii).

16. The nucleic acid sequence of claim 15, wherein the nucleic acid sequence hybridizes under medium stringency with (i) nucleotides 135 to 2425 of SEQ ID NO:1, (ii) the genomic sequence comprising nucleotides 135 to 2425 of SEQ ID NO:1, or (iii) a complementary strand of (i) or (ii).

17. The nucleic acid sequence of claim 1, wherein the nucleic acid sequence hybridizes under high stringency conditions with (i) nucleotides 135 to 2425 of SEQ ID NO.1, (ii) the genomic sequence comprising nucleotides 135 to 2425 of SEQ ID NO:1, (iii) a subsequence of (i) or (ii) of at least 100 nucleotides, or (iv) a complementary strand of (i), (ii), or (iii).

18. The nucleic acid sequence of claim 17, wherein the nucleic acid sequence hybridizes under high stringency conditions with (i) nucleotides 135 to 2425 of SEQ ID NO:1, (ii) the genomic sequence comprising nucleotides 135 to 2425 of SEQ ID NO:1, or (iii) a complementary strand of (i) or (ii).

19. The nucleic acid sequence of claim 1, which encodes the polypeptide of SEQ ID NO:2 having cellobiose dehydrogenase activity with a pH optimum at a pH of about 5–9 using DCPIP or benzoquinones as the electron acceptor, about pH 7–9 using cytochrome C as the electron acceptor, and about pH 9 using ferric cyanide as the electron acceptor; a temperature optimum of 55° C. at pH 9.5, a molecular weight of about 92 kDa by SDS-PAGE; an isoelectric point of about 4–5; a relative activity of at least 70% at a pH of about 9 and a temperature of about 50° C.; and stability at a pH of 5–10.

20. The nucleic acid sequence of claim 1, which is contained in the plasmid pEJG44 which is contained in *Escherichia coli* NRRL B-30065.

21. A nucleic acid construct comprising the nucleic acid sequence of claim 1 operably linked to one or more control sequences which direct the production of the polypeptide in a suitable expression host.

22. A recombinant expression vector comprising the nucleic acid construct of claim 21.

23. A recombinant host cell comprising the nucleic acid construct of claim 21.

24. A method for producing a polypeptide having cellobiose dehydrogenase activity comprising (a) cultivating the host cell of claim 23 under conditions suitable for production of the polypeptide; and (b) recovering the polypeptide.

25. A nucleic acid construct comprising a gene encoding a protein operably linked to a nucleic acid sequence encoding a signal peptide consisting of nucleotides 71 to 134 of SEQ ID NO.1, wherein the gene is foreign to the nucleic acid sequence.

26. A recombinant expression vector comprising the nucleic acid construct of claim 25.

27. A recombinant host cell comprising the nucleic acid construct of claim 25.

28. A method for producing a protein comprising (a) cultivating the recombinant host cell of claim 27 under conditions suitable for production of the protein; and (b) recovering the protein.

* * * * *

SEQUENCE LISTING

<160> NUMBER OF SEQ ID NOS: 4

<210> SEQ ID NO 1
<211> LENGTH: 2576
<212> TYPE: DNA
<213> ORGANISM: Humicola

<400> SEQUENCE: 1

```
agctacagct tccttgggcc cgtctgaacc aaccttctgg gaccaagtgg tgagatctgg      60
cggcacaacc atgaagttcc tcggccgtat tggggcgacc gcccttgcgg cgtcgctgta     120
tctcacatca ggcgccgcgc aagccactgg tgatgcgtac accgactcgg aaacaggcat     180
taagttccag acctggtccc cggatccgca gttcactttt ggccttgccc tgccgccgga     240
tgccctggag aaggatgcca ctgagtacat tggtcttctc cgctgcacca gggccgaccc     300
atccgaccct ggctactgcg gtctctctca tggccaggtc ggccagatga cgcagtcgct     360
gcttctcgtg gcctgggcct acgagaacca ggtctacacg tcgttccgct acgccaccgg     420
ctacaccctc ccgggtctgt acaccggcaa cgctaagctg acccagctct ccgtcaacat     480
caccgacacc agcttcgagc tcatctaccg ctgcgagaac tgcttctcgt gggagcacga     540
aggcagcacc ggatctagct cgacctccca gggctatctc gtcctcggtc gtgcttccgc     600
ccgccgcggc gtcgtcggcc cgacttgccc ggacacggcc acctttggtt tccacgacaa     660
tggcttcggt cagtggggtg ttggtctcga gaatgccgtt tcggagcagt attctgagtg     720
```

-continued

```
ggcttcgctg ccgggtctga ctgttgagac cacctgcgaa ggatccggcc ctggtgaggc      780
gcagtgcgtg cctgcccctg aggagactta tgactatatt gttgttggtg ctggcgccgg      840
cggtattcct gtcgccgaca agctgagcga ggccggccac aaggttctgc tcatcgagaa      900
gggtcccccg tcgacgggcc gctggcaggg taccatgaag cccgagtggc ttgaaggcac      960
tgacctcact cggttcgatg tgcccggcct ttgcaaccaa atctgggttg actcggctgg     1020
cattgcctgc actgatactg atcagatggc tggctgcgtc ttgggcggtg cacggccgt     1080 taatgctggc ctgtggtgga agcccattga cctcgactgg gatgagaact ccctgaggg     1140 ctggcactcg caggatctcg ccgcggcgac cgagcgcgtc tttgagcgca tccccggcac     1200
ctggcacccg tccatggatg gcaagctgta ccgtgacgaa ggctacaagg ttctctccag     1260
cggtctggct gagtctggct ggaaggaggt tgtggccaac gaggttccca acgagaagaa     1320
ccgcactttc gcccacaccc acttcatgtt cgctggcgga gagcgtaacg ggcctcttgc     1380
cacttacctg gtctctgccg atgcccgcga gaacttctcg ctctggacca cactgctgt     1440 tcgccgcgct gtccgcactg gtggcaaggt cacaggtgtc gagctcgagt gcttgactga     1500
tggcggctac agcggcattg ttaagctcaa tgagggcggt ggcgtcatct tctcggccgg     1560
tgcctttggt tcggccaagc tgctcttccg cagcggtatc ggccctgagg atcagctccg     1620
cgttgttgcc tcctctaagg acggagagga cttcatcgac gagaaggact ggattaagct     1680
ccccgtcggc tacaacctga ttgaccacct taacactgac ctcatcctca ctcaccccga     1740
tgtcgtcttc tacgacttct atgaggcctg gaccaccccg atcgaggccg acaagcagct     1800
gtaccttgag cagcgctctg gcatccttgc ccaggctgct cctaacattg gccccatgat     1860
gtgggagcag gtcaccccct cggacggcat tacccgccaa ttccagtgga cggctcgcgt     1920
cgagggcgac agccgcttca ccaactcttc tcatgccatg actctcagcc agtacctcgg     1980
ccgtggtgtc gtgtcgcgcg gtcgcgccac catcacccag ggtctcgtca ccaccgtggc     2040
tgagcacccg tacctccaca acgccggcga caaggaggcc gtcattcagg gcatcaagaa     2100
cctcattgag tctcttaacg tgattcccaa catcacttgg gtcctgccgc tcctggtag      2160 cactgtcgag gaatacgtcg attcgctcct cgtctccgcc tcggctcgtc gctcgaacca     2220
ctggatgggc acgccaagc tgggtactga tgatggccgc tacggcggta cttcggtcgt      2280
cgacctcgac accaaggtct acggcaccga taacctgttc gtggtggatg cttccatctt     2340
ccctggcatg tcgaccggca acccgtccgc tatgatcgtg attgccgctg agcaggctgc     2400
ggagcgcatt cttaagctga ggaagtaaga aggggagaga ggatggaggg atgacattga     2460
ggaaaatagg gttatgagtt gatgagttat gggcgaatgt gtcagccagt gtacttgact     2520
tattacctga gttaaacaac acgacgtgct tgatgtgtta aaaaaaaaa aactt          2576
```

<210> SEQ ID NO 2
<211> LENGTH: 785
<212> TYPE: PRT
<213> ORGANISM: Humicola

<400> SEQUENCE: 2

Met Lys Phe Leu Gly Arg Ile Gly Ala Thr Ala Leu Ala Ala Ser Leu
 1               5                  10                  15

Tyr Leu Thr Ser Gly Ala Ala Gln Ala Thr Gly Asp Ala Tyr Thr Asp
            20                  25                  30

Ser Glu Thr Gly Ile Lys Phe Gln Thr Trp Ser Pro Asp Pro Gln Phe
        35                  40                  45

-continued

```
Thr Phe Gly Leu Ala Leu Pro Pro Asp Ala Leu Glu Lys Asp Ala Thr
     50                  55                  60
Glu Tyr Ile Gly Leu Leu Arg Cys Thr Arg Ala Asp Pro Ser Asp Pro
 65                  70                  75                  80
Gly Tyr Cys Gly Leu Ser His Gly Gln Val Gly Gln Met Thr Gln Ser
                 85                  90                  95
Leu Leu Leu Val Ala Trp Ala Tyr Glu Asn Gln Val Tyr Thr Ser Phe
            100                 105                 110
Arg Tyr Ala Thr Gly Tyr Thr Leu Pro Gly Leu Tyr Thr Gly Asn Ala
            115                 120                 125
Lys Leu Thr Gln Leu Ser Val Asn Ile Thr Asp Thr Ser Phe Glu Leu
130                 135                 140
Ile Tyr Arg Cys Glu Asn Cys Phe Ser Trp Glu His Glu Gly Ser Thr
145                 150                 155                 160
Gly Ser Ser Ser Thr Ser Gln Gly Tyr Leu Val Leu Gly Arg Ala Ser
                165                 170                 175
Ala Arg Arg Gly Val Val Gly Pro Thr Cys Pro Asp Thr Ala Thr Phe
            180                 185                 190
Gly Phe His Asp Asn Gly Phe Gly Gln Trp Gly Val Gly Leu Glu Asn
            195                 200                 205
Ala Val Ser Glu Gln Tyr Ser Glu Trp Ala Ser Leu Pro Gly Leu Thr
210                 215                 220
Val Glu Thr Thr Cys Glu Gly Ser Gly Pro Gly Glu Ala Gln Cys Val
225                 230                 235                 240
Pro Ala Pro Glu Glu Thr Tyr Asp Tyr Ile Val Val Gly Ala Gly Ala
                245                 250                 255
Gly Gly Ile Pro Val Ala Asp Lys Leu Ser Glu Ala Gly His Lys Val
            260                 265                 270
Leu Leu Ile Glu Lys Gly Pro Pro Ser Thr Gly Arg Trp Gln Gly Thr
            275                 280                 285
Met Lys Pro Glu Trp Leu Glu Gly Thr Asp Leu Thr Arg Phe Asp Val
290                 295                 300
Pro Gly Leu Cys Asn Gln Ile Trp Val Asp Ser Ala Gly Ile Ala Cys
305                 310                 315                 320
Thr Asp Thr Asp Gln Met Ala Gly Cys Val Leu Gly Gly Gly Thr Ala
                325                 330                 335
Val Asn Ala Gly Leu Trp Trp Lys Pro Ile Asp Leu Asp Trp Asp Glu
            340                 345                 350
Asn Phe Pro Glu Gly Trp His Ser Gln Asp Leu Ala Ala Ala Thr Glu
            355                 360                 365
Arg Val Phe Glu Arg Ile Pro Gly Thr Trp His Pro Ser Met Asp Gly
370                 375                 380
Lys Leu Tyr Arg Asp Glu Gly Tyr Lys Val Leu Ser Ser Gly Leu Ala
385                 390                 395                 400
Glu Ser Gly Trp Lys Glu Val Ala Asn Glu Val Pro Asn Glu Lys
                405                 410                 415
Asn Arg Thr Phe Ala His Thr His Phe Met Phe Ala Gly Gly Glu Arg
            420                 425                 430
Asn Gly Pro Leu Ala Thr Tyr Leu Val Ser Ala Asp Ala Arg Glu Asn
            435                 440                 445
Phe Ser Leu Trp Thr Asn Thr Ala Val Arg Arg Ala Val Arg Thr Gly
450                 455                 460
Gly Lys Val Thr Gly Val Glu Leu Glu Cys Leu Thr Asp Gly Gly Tyr
```

```
465                 470                 475                 480
Ser Gly Ile Val Lys Leu Asn Glu Gly Gly Val Ile Phe Ser Ala
                    485                 490                 495

Gly Ala Phe Gly Ser Ala Lys Leu Leu Phe Arg Ser Gly Ile Gly Pro
                500                 505                 510

Glu Asp Gln Leu Arg Val Val Ala Ser Ser Lys Asp Gly Glu Asp Phe
                515                 520                 525

Ile Asp Glu Lys Asp Trp Ile Lys Leu Pro Val Gly Tyr Asn Leu Ile
            530                 535                 540

Asp His Leu Asn Thr Asp Leu Ile Leu Thr His Pro Asp Val Val Phe
545                 550                 555                 560

Tyr Asp Phe Tyr Glu Ala Trp Thr Thr Pro Ile Glu Ala Asp Lys Gln
                565                 570                 575

Leu Tyr Leu Glu Gln Arg Ser Gly Ile Leu Ala Gln Ala Pro Asn
                580                 585                 590

Ile Gly Pro Met Met Trp Glu Gln Val Thr Pro Ser Asp Gly Ile Thr
            595                 600                 605

Arg Gln Phe Gln Trp Thr Ala Arg Val Glu Gly Asp Ser Arg Phe Thr
                610                 615                 620

Asn Ser Ser His Ala Met Thr Leu Ser Gln Tyr Leu Gly Arg Gly Val
625                 630                 635                 640

Val Ser Arg Gly Arg Ala Thr Ile Thr Gln Gly Leu Val Thr Thr Val
                645                 650                 655

Ala Glu His Pro Tyr Leu His Asn Ala Gly Asp Lys Glu Ala Val Ile
                660                 665                 670

Gln Gly Ile Lys Asn Leu Ile Glu Ser Leu Asn Val Ile Pro Asn Ile
                675                 680                 685

Thr Trp Val Leu Pro Pro Gly Ser Thr Val Glu Glu Tyr Val Asp
            690                 695                 700

Ser Leu Leu Val Ser Ala Ser Ala Arg Arg Ser Asn His Trp Met Gly
705                 710                 715                 720

Thr Ala Lys Leu Gly Thr Asp Asp Gly Arg Tyr Gly Gly Thr Ser Val
                725                 730                 735

Val Asp Leu Asp Thr Lys Val Tyr Gly Thr Asp Asn Leu Phe Val Val
            740                 745                 750

Asp Ala Ser Ile Phe Pro Gly Met Ser Thr Gly Asn Pro Ser Ala Met
            755                 760                 765

Ile Val Ile Ala Ala Glu Gln Ala Ala Glu Arg Ile Leu Lys Leu Arg
            770                 775                 780

Lys
785

<210> SEQ ID NO 3
<211> LENGTH: 26
<212> TYPE: DNA
<213> ORGANISM: Humicola
<220> FEATURE:
<221> NAME/KEY: misc_feature
<222> LOCATION: (0)...(0)
<223> OTHER INFORMATION: r= a or g, y= c or t, m= a or c, n= Inosine

<400> SEQUENCE: 3
atggayggna arytntaymg ngayga                                    26

<210> SEQ ID NO 4
<211> LENGTH: 20
```

-continued

```
<212> TYPE: DNA
<213> ORGANISM: Humicola
<220> FEATURE:
<221> NAME/KEY: misc_feature
<222> LOCATION: (0)...(0)
<223> OTHER INFORMATION: r= a or g, y= c or t, k= g or t, n= Inosine

<400> SEQUENCE: 4
aarttytcnc kngcrtcngc                                                20
```